(12) United States Patent
Tanaka et al.

(10) Patent No.: US 11,844,496 B2
(45) Date of Patent: Dec. 19, 2023

(54) IMAGING SYSTEM

(71) Applicant: OLYMPUS CORPORATION, Hachioji (JP)

(72) Inventors: Takanori Tanaka, Tokyo (JP); Masato Osawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 466 days.

(21) Appl. No.: 17/189,773

(22) Filed: Mar. 2, 2021

(65) Prior Publication Data

US 2021/0177241 A1    Jun. 17, 2021

Related U.S. Application Data

(63) Continuation of application No. PCT/JP2019/000378, filed on Jan. 9, 2019.

(51) Int. Cl.
*A61B 1/00* (2006.01)
*A61B 1/045* (2006.01)
*H04N 7/18* (2006.01)
*H04N 23/60* (2023.01)

(52) U.S. Cl.
CPC ...... *A61B 1/00006* (2013.01); *A61B 1/00009* (2013.01); *A61B 1/00013* (2013.01); *A61B 1/045* (2013.01); *H04N 7/18* (2013.01); *H04N 23/60* (2023.01)

(58) Field of Classification Search
CPC ............ A61B 1/00006; A61B 1/00009; A61B 1/00013; A61B 1/045; A61B 1/00011; H04N 7/18; H04N 23/60; H04N 23/00; H04N 23/66; H04N 7/183; H04N 23/555
See application file for complete search history.

(56) References Cited

U.S. PATENT DOCUMENTS

2009/0058997 A1\*  3/2009  Kato ..................... H04N 7/183
                                                    348/E7.085
2019/0125168 A1\*  5/2019  Kobayashi ......... A61B 1/00186
2019/0342481 A1\* 11/2019  Sorgius ................ H05B 47/125

FOREIGN PATENT DOCUMENTS

JP      2008-68021 A       3/2008
JP      2009-61032 A       3/2009
JP     2018-192086 A      12/2018

OTHER PUBLICATIONS

International Search Report dated Feb. 12, 2019, issued in counterpart International Application No. PCT/JP2019/000378, w/English translation (2 pages).

\* cited by examiner

*Primary Examiner* — Michael E Teitelbaum
(74) *Attorney, Agent, or Firm* — WHDA, LLP

(57) ABSTRACT

In an imaging system, an image transmission circuit is configured to output image data to a signal line in a first mode. A signal reception circuit is configured to receive a clock control signal for adjusting a frequency of a camera clock from an image reception unit in a second mode. A signal output circuit is configured to output a first electric potential and the clock control signal to the signal line. The first electric potential corresponds to a signal level that is not included in a range of a signal level of the image data output to the signal line. A communication control circuit is configured to switch communication modes from the first mode to the second mode when the communication control circuit detects the first electric potential in the first mode.

15 Claims, 14 Drawing Sheets

IMAGING SYSTEM

The present application is a continuation application based on International Patent Application No. PCT/JP2019/000378 filed on Jan. 9, 2019, the content of which is incorporated herein by reference.

BACKGROUND OF THE INVENTION

Field of the Invention

The present invention relates to an imaging system.

Description of Related Art

An imaging system including two units is disclosed in Japanese Unexamined Patent Application, First Publication No. 2008-068021. This imaging system includes a first unit including an imager and a second unit that receives image data transmitted from the first unit. The two units are connected to each other by a signal line for transmitting the image data. The first unit transmits the image data to the second unit in an image-signal period. The second unit transmits a control signal to the first unit in a blanking period of the imager.

SUMMARY OF THE INVENTION

According to a first aspect of the present invention, an imaging system includes a camera unit and an image reception unit. The camera unit includes an imager, a communication control circuit, an image transmission circuit, a signal reception circuit, and a clock adjustment circuit. The imager is configured to generate image data on the basis of a camera clock. The communication control circuit is configured to detect an electric potential of a signal line and switch communication modes between a first mode and a second mode on the basis of the detected electric potential. The image transmission circuit is configured to output the image data 10 the signal line in the first mode. The signal reception circuit is electrically connected to the signal line and is configured to receive a clock control signal for adjusting a frequency of the camera clock from the image reception unit in the second mode. The clock adjustment circuit is configured to adjust the frequency of the camera clock on the basis of the clock control signal. The image reception unit includes an image reception circuit and a signal output circuit. The image reception circuit is electrically connected to the signal line and is configured to receive the image data. The signal output circuit is configured to output a first electric potential and the clock control signal to the signal line. The first electric potential corresponds to a signal level that is not included in a range of a signal level of the image data output to the signal line. The communication control circuit is configured to switch the communication modes from the first mode to the second mode when the communication control circuit detects the first electric potential in the first mode.

According to a second aspect of the present invention, in the first aspect, the signal output circuit may be configured to output a communication control signal indicating an instruction to switch the communication modes from the second mode to the first mode to the signal line after the signal output circuit outputs the first electric potential to the signal line. The communication control circuit may be configured to switch the communication modes from the second mode to the first mode when the communication control circuit detects the communication control signal on the signal line in the second mode.

According to a third aspect of the present invention, in the second aspect, the clock control signal may be a pulse signal indicating a system clock of the image reception unit. A pattern of a signal level of the pulse signal may correspond to data of the communication control signal.

According to a fourth aspect of the present invention, in the first aspect, the signal output circuit may be configured to output a second electric potential to the signal line after the signal output circuit outputs the first electric potential to the signal line. The second electric potential may correspond to a signal level included in the range of the signal level of the image data. The communication control circuit may be configured to switch the communication modes from the second mode to the first mode when the communication control circuit detects the second electric potential in the second mode.

According to a fifth aspect of the present invention, in any one of the first to fourth aspects, the camera unit and the image reception unit may be connected to each other by the signal line, a first power source line, and a second power source line. The first power source line may be configured to transmit a power source voltage that is to be supplied to the imager from the image reception unit to the camera unit. The second power source line may be configured to transmit a substrate voltage that is to be supplied to the imager from the image reception unit to the camera unit. The substrate voltage may be lower than the power source voltage. The camera unit may further include a first pad electrically connected to the signal line, a second pad electrically connected to the first power source line, and a third pad electrically connected to the second power source line. The camera unit may be electrically connected to the image reception unit via only the first pad, the second pad, and the third pad.

According to a sixth aspect of the present invention, in the fifth aspect, the image transmission circuit may include a source follower circuit including a transistor. The transistor may include a first terminal to which the image data or the substrate voltage is input, a second terminal to which the power source voltage is input, and a third terminal. The image data may be input to the first terminal in the first mode. The third terminal may output a third electric potential corresponding to the signal level of the image data to the signal line in the first mode. A maximum value of the third electric potential may be less than or equal to a voltage lower than the power source voltage by a threshold voltage of the transistor. A minimum value of the third electric potential may be greater than or equal to the substrate voltage. The communication control circuit may be configured to switch the communication modes from the first mode to the second mode by causing input of the image data to the first terminal to be stopped and causing input of the substrate voltage to the first terminal to be started when the communication control circuit detects the first electric potential higher than the maximum value in the first mode.

According to a seventh aspect of the present invention, in the fifth aspect, the image transmission circuit may include a source follower circuit including a transistor. The transistor may include a first terminal to which the image data or the substrate voltage is input, a second terminal to which the substrate voltage is input, and a third terminal. The image data may be input to the first terminal in the first mode. The third terminal may output a third electric potential corresponding to the signal level of the image data to the signal line in the first mode. A maximum value of the third electric potential may be less than or equal to the power source voltage. A minimum value of the third electric potential may be greater than or equal to a voltage higher than the substrate voltage by a threshold voltage of the transistor. The communication control circuit may be configured to switch the communication modes from the first mode to the second mode by causing input of the image data to the first terminal to be stopped and causing input of the power source voltage to the first terminal to be started when the communication control circuit detects the first electric potential lower than the minimum value in the first mode.

According to an eighth aspect of the present invention, in any one of the first to seventh aspects, the imaging system may further include a first switch. The image reception circuit may include a DC termination resistor configured to operate when the image data are received. The first switch may be configured to electrically connect the signal line and the DC termination resistor together when the image reception circuit receives the image data. The first switch may be configured to electrically disconnect the signal line and the DC termination resistor from each other when the signal output circuit outputs the first electric potential to the signal line.

According to a ninth aspect of the present invention, in the eighth aspect, the imaging system may further include a second switch. The image reception circuit may include an AC termination resistor and a DC-cutting condenser. The DC-cutting condenser may be connected to the signal line and the AC termination resistor and may be configured to cut DC components of an electric potential of the signal line when the image data are received. The second switch may be configured to electrically connect the signal line and the AC termination resistor together and electrically connect the signal line and the DC-cutting condenser together when the image reception circuit receives the image data. The second switch may be configured to electrically disconnect the signal line and the AC termination resistor from each other and electrically disconnect the signal line and the DC-cutting condenser from each other when the signal output circuit outputs the first electric potential to the signal line.

According to a tenth aspect of the present invention, in any one of the first to ninth aspects, the signal output circuit may be configured to output the clock control signal to the signal line in a blanking period of the imager.

According to an eleventh aspect of the present invention, in any one of the first to tenth aspects, the signal output circuit may be configured to output a negative voltage that is not included in the range of the signal level of the image data to the signal line. The camera unit may further include a voltage supply circuit that is electrically connected to the signal line and is configured to supply the negative voltage to the imager in the second mode.

According to a twelfth aspect of the present invention, in the eleventh aspect, the signal output circuit may be configured to output the negative voltage to the signal line in a horizontal blanking period of the imager and output the clock control signal to the signal line in a vertical blanking period of the imager.

According to a thirteenth aspect of the present invention, in any one of the first to twelfth aspects, the clock control signal may be a pulse signal having a cycle that is integer limes longer than a cycle of a system clock of the image reception unit. The clock adjustment circuit may be configured to synchronize the camera clock with the pulse signal.

According to a fourteenth aspect of the present invention, in any one of the first to twelfth aspects, the clock control signal may be an analog signal having a voltage corresponding to a frequency of a system clock of the image reception unit. The clock adjustment circuit may include a voltage-controlled oscillator (VCO) configured to generate the camera clock having a frequency corresponding to a voltage of the clock control signal.

According to a fifteenth aspect of the present invention, in any one of the first to twelfth aspects, the clock control signal may be a digital signal indicating a value corresponding to a frequency of a system clock of the image reception unit. The clock adjustment circuit may include a digital-to-analog converter (DAC) circuit and a voltage-controlled oscillator (VCO). The DAC circuit may be configured to generate an analog signal having a voltage corresponding to the value indicated by the clock control signal. The VCO may be configured to generate the camera clock having frequency corresponding to the voltage of the analog signal.

DETAILED DESCRIPTION OF THE INVENTION

Hereinafter, embodiments of the present invention will be described with reference to the drawings. Each embodiment will be described in detail using an endoscope system as an example of an image system.

First Embodiment

Figure 1:
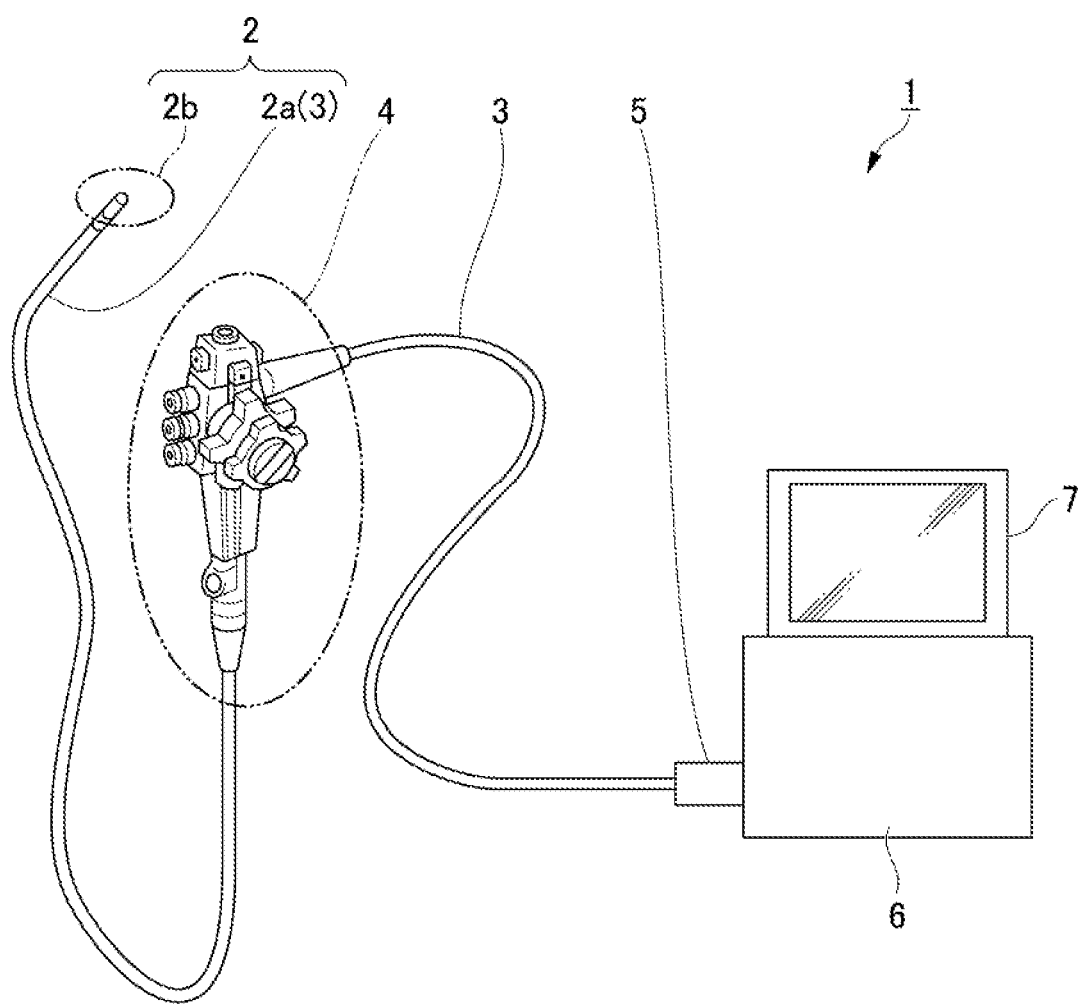
FIG. 1 is a schematic diagram showing a configuration of an endoscope system according to a first embodiment of the present invention.

FIG. 1 shows a configuration of an endoscope system 1 according to a first embodiment of the present invention. The endoscope system 1 shown in FIG. 1 includes an endoscope insertion unit 2, a transmission cable 3, an operation unit 4, a connector unit 5, a processor 6, and a display device 7. The endoscope insertion unit 2, the transmission cable 3, the operation unit 4, and the connector unit 5 constitute an endoscope.

The endoscope insertion unit 2 includes an insertion unit 2a. The insertion unit 2a is part of the transmission cable 3. The insertion unit 2a is to be inserted inside a subject. The endoscope insertion unit 2 generates image data by imaging the inside of the subject. The endoscope insertion unit 2 outputs the generated image data to the processor 6. A camera unit 10 is disposal in a distal end 2b of the insertion unit 2a shown in FIG. 2. In the insertion unit 2a, the operation unit 4 is connected to the end part opposite to the distal end 2b. The operation unit 4 accepts various operations for the endoscope insertion unit 2 from a user.

The transmission cable 3 connects the camera unit 10 and the connector unit 5 together. The image data generated by the camera unit 10 are output to the connector unit 5 via the transmission cable 3.

The connector unit 5 is connected to the endoscope insertion unit 2 and the processor 6. The connector unit 5 performs predetermined processing on the image data output from the endoscope insertion unit 2. The connector unit 5 outputs the image data to the processor 6.

The processor 6 performs predetermined image-processing on the image data output from the connector unit 5. Furthermore, the processor 6 centrally controls the entire endoscope system 1.

The display device 7 displays an image on the basis of the image data processed by the processor 6. In addition, the display device 7 displays various pieces of information related to the endoscope system 1.

The endoscope system 1 includes a light source device that generates illumination light emitted to the subject. The light source device is not shown in FIG. 1.

Figure 2:
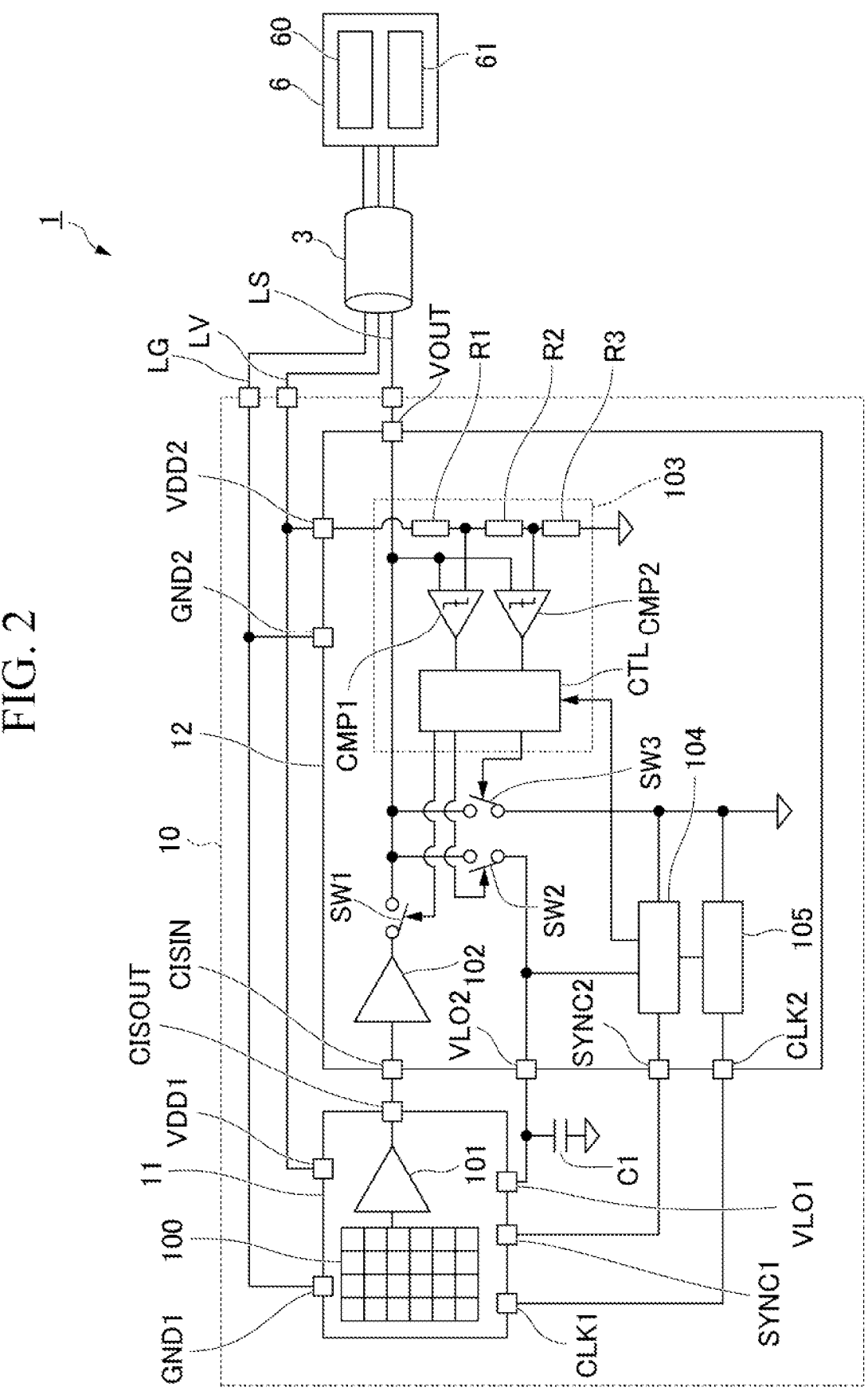
FIG. 2 is a block diagram showing a configuration of the endoscope system according to the first embodiment of the present invention.

FIG. 2 shows an internal configuration of the endoscope system 1. The endoscope system 1 shown in FIG. 2 includes the camera unit 10 and the processor 6. The operation unit 4, the connector unit 5, and the display device 7 are not shown in FIG. 2.

The processor 6 is an image reception unit. The camera unit 10 and the processor 6 are connected to each other by a signal line LS, a power source line LV, and a ground line LG. The signal line LS, the power source line LV, and the ground line LG pass through the transmission cable 3.

A schematic configuration of the endoscope system 1 will be described. The camera unit 10 includes an imager 11, a communication control circuit 103, a buffer 101 (image transmission circuit), a switch SW3 (signal reception circuit), and a voltage-controlled oscillator (VCO) 105 (clock adjustment circuit). The imager 11 generates image data on the basis of a camera clock that is a clock generated in the camera unit 10. The communication control circuit 103 detects an electric potential of the signal line LS. The communication control circuit 103 switches communication modes between a first mode and a second mode on the basis of the detected electric potential. The buffer 101 outputs the image data to the signal line LS in the first mode. The switch SW3 is electrically connected to the signal line LS. The switch SW3 is turned on or short-circuited in live second mode, receives a clock control signal for adjusting a frequency of the camera clock from the processor 6, and leads the clock control signal to the VCO 105. The VCO 105 adjusts the frequency of the camera clock on the basis of the clock control signal.

The processor 6 includes an image reception circuit 60 and a signal output circuit 61. The image reception circuit 60 and the signal output circuit 61 are electrically connected to the signal line LS. The image reception circuit 60 receives the image data. The signal output circuit 61 outputs a first electric potential and the clock control signal to the signal line LS. The first electric potential corresponds to a signal level (voltage level) that is not included in a range of a signal level of the image data output to the signal line LS. When the communication control circuit 103 detects the first electric potential in the first mode, the communication control circuit 103 switches the communication modes from the first mode to the second mode. All or part of the image reception circuit 60 and the signal output circuit 61 may be disposed in the operation unit 4 or the connector unit 5.

The first mode is a communication mode for transmitting the image data from the camera unit 10 to the processor 6. The second mode is a communication mode for transmitting the clock control signal and a negative voltage from the processor 6 to the camera unit 10. The clock control signal in the first embodiment is an analog signal having a voltage corresponding to the frequency of the system clock of the processor 6. The clock control signal has the first electric potential corresponding to the signal level that is not included in the range of the signal level of the image data output to the signal line LS. The negative voltage is not included in the range of the signal level of the image data output to the signal line LS. The negative voltage is supplied to the imager 11. When the communication control circuit 103 detects the negative voltage in the first mode, the communication control circuit 103 switches the communication modes from the first mode to the second mode.

A derailed configuration of the endoscope system 1 will be described. The camera unit 10 includes the imager 11 and a control unit 12. The imager 11 is an imaging device (image sensor). The imager 11 includes a pixel unit 100 and the buffer 101.

The pixel unit 100 includes a plurality of pixels. The pixel unit 100 generates a pixel signal on the basis of light incident to the pixel unit 100. The imager 11 performs noise suppression, signal amplification, and the like on the pixel signal by using a circuit not shown in FIG. 2 and generates image data. The buffer 101 is used for enhancing the driving performance of the input image data and is used for outputting the image data to the outside (control unit 12). When the communication mode is the first mode, the buffer 101 outputs the image data to the control unit 12. The buffer 101 outputs the image data to the signal line LS via the control unit 12.

The imager 11 includes a pad VDD1, a pad GND1, a pad CISOUT, a pad VLO1, a pad SYNC1, and a pad CLK1 in addition to the pixel unit 100 and the buffer 101. The pad VDD1 is connected to the power source line LV. The power source line LV transmits a power source voltage from the processor 6 to the camera unit 10. The power source voltage is input to the pad VDD1. The pad GND1 is connected to the ground line LG. The ground line LG transmits a ground voltage from the processor 6 to the camera unit 10. The ground voltage is input to the pad GND1.

The negative voltage for reducing a dark current generated in the pixel unit 100 of the imager 11 is input to the pad VLO1. This negative voltage is used by the communication control circuit 103 to control the state of the communication mode on the control unit 12 side. The control signal for controlling reading of the pixel signal in the imager 11 is input to the pad SYNC1. The camera clock is input to the pad CLK1. The signal input to each pad of the imager 11 is supplied to the circuits in the imager 11. The imager 11 operates in synchronization with the camera clock.

The pad CISOUT is connected to the buffer 101. The image data output from the buffer 101 are transferred to the control unit 12 via the pad CISOUT.

The control unit 12 includes a buffer 102, the communication control circuit 103, a timing generator 104, the VCO 103, a switch SW1, a switch SW2, and the switch SW3. A capacitance element C1 is connected to the imager 11 and the control unit 12.

The buffer 102 is connected to the imager 11. The image data output from the imager 11 are input to the buffer 102. When the communication mode is the first mode, the switch SW1 is in the ON (short-circuited) state and the buffer 102 outputs the image data to the signal line LS via the switch SW1.

Each of the switch SW1, the switch SW2, and the switch SW3 includes a first terminal and a second terminal. The state of each of the switch SW1, the switch SW2, and the switch SW3 becomes any one of the ON (short-circuited) state and the OFF (open-circuited) state. When the state of each switch is the ON (short-circuited) state, the first terminal and the second terminal are electrically connected to each other. When the state of each switch is the OFF (open-circuited) state, the first terminal and the second terminal are electrically insulated from each other.

The first terminal of the switch SW1 is connected to the buffer 102 and the second terminal of the switch SW1 is connected to the signal line LS. When the communication mode is the first mode, the state of the switch SW1 becomes the ON state. At this time, the image data are output from the buffer 102 to the signal line LS. When the communication mode is the second mode, the state of the switch SW1 becomes the OFF state. At this time, the image data are not output from the buffer 102 to the signal line LS.

The first terminal of the switch SW2 is connected to the signal line LS and the second terminal of the switch SW2 is connected to the capacitance element C1. When the communication mode is the second mode, the state of the switch SW2 becomes the ON state. At this time, the negative voltage is output from the signal line LS to the capacitance element C1. The switch SW2 receives the negative voltage from the processor 6. When the communication mode is the first mode, the state of the switch SW2 becomes the OFF state.

The first terminal of the switch SW3 is connected to the signal line LS and the second terminal of the switch SW3 is connected to the timing generator 104 and the VCO 105. When the communication mode is the second mode, the state of the switch SW3 becomes the ON state. At this time, the clock control signal is output from the signal line LS to the timing generator 104 and the VCO 105. The switch SW3 receives the clock control signal from the processor 6. When the communication mode is the first mode, the state of the switch SW3 becomes the OFF state.

The communication control circuit 103 includes a controller CTL, a comparator CMP1, a comparator CMP2, a resistor R1, a resistor R2, and a resistor R3. Each of the resistor R1, the resistor R2, and the resistor R3 includes a first terminal and a second terminal. The first terminal of the resistor R1 is connected to the power source line LV. The power source voltage is input to the first terminal of the resistor R1. The first terminal of the resistor R2 is connected to the second terminal of the resistor R1. The first terminal of the resistor R3 is connected to the second terminal of the resistor R2. The ground voltage is input to the second terminal of the resistor R3. The resistor R1, the resistor R2, and the resistor R3 generate a voltage that is based on the power source voltage, the ground voltage, and the resistance value of each resistor.

Each of the comparator CMP1 and the comparator CMP2 includes a first input terminal, a second input terminal, and an output terminal. The first input terminal of the comparator CMP1 is connected to the signal line LS. The second input terminal of the comparator CMP1 is connected to the second terminal of the resistor R1. The output terminal of the comparator CMP1 is connected to the controller CTL. The first input terminal of the comparator CMP2 is connected to the signal line LS. The second input terminal of the comparator CMP2 is connected to the second terminal of the resistor R2. The output terminal of the comparator CMP2 is connected to the controller CTL.

Each of the comparator CMP1 and the comparator CMP2 compares the voltage input to the first input terminal with the voltage input to the second input terminal. In other words, each of the comparator CMP1 and the comparator CMP2 compares the electric potential of the signal line LS with a predetermined electric potential. Each of the comparator CMP1 and the comparator CMP2 outputs a signal indicating the comparison results to the controller CTL.

The controller CTL detects the electric potential of the signal line LS on the basis of the signal output from each of the comparator CMP1 and the comparator CMP2. The controller CTL generates a control signal for controlling the state of each of the switch SW1, the switch SW2, and the switch SW3 on the basis of the detected electric potential. The controller CTL outputs the generated control signal to each of the switch SW1, the switch SW2, and the switch SW3. The controller CTL switches the communication modes of the camera unit 10 between the first mode and the second mode.

The timing generator 104 is connected to the second terminal of the switch SW2, the second terminal of the switch SW3, and the VCO 105. When the communication mode is the second mode, the negative voltage is input to the timing generator 104 via the switch SW2. Alternatively, when the communication mode is the second mode, the clock control signal is input to the liming generator 104 via the switch SW2. The camera clock is input to the timing generator 104 from the VCO 105 at all times.

The timing generator 104 includes a counter. The timing generator 104 starts execution of clock-counting of the camera clock at the timing at which the negative voltage or the clock control signal is input to the timing generator 104 as a starting point. The timing generator 104 outputs a control signal for controlling reading of the pixel signal in the imager 11 to the imager 11 on the basis of the counted value. In addition, when a predetermined number is counted, the timing generator 104 outputs a control signal for switching the communication modes from the second mode to the first mode to the controller CTL.

The VCO 105 is connected to the second terminal of the switch SW3. When the communication mode is the second mode, the clock control signal is input to the VCO 105 via the switch SW2. The VCO 105 generates the camera clock having a frequency corresponding to the voltage of the clock control signal. The VCO 105 outputs the generated camera clock to the imager 11. When the communication mode is the second mode, the VCO 105 adjusts the frequency of the camera clock. When the communication mode is the first mode, the VCO 105 generates the camera clock having a frequency that has been set in the second mode.

The control unit 12 includes a pad VDD2, a pad GND2, a pad CISIN, a pad VOUT, a pad VLO2, a pad SYNC2, and a pad CLK2 in addition to the buffer 102 and the like. The pad VDD2 is connected to the power source fine LV. The power source voltage is input to the pad VDD2. The pad GND2 is connected to the ground line LG. The ground voltage is input to the pad GND2.

The pad CISIN is connected to the pad CISOUT and the buffer 102. The image data are output from the pad CISOUT and are input to the pad CISIN. The image data are output to the buffer 102 via the pad CISIN.

The pad VOUT is connected to the second terminal of the switch SW1, the first terminal of the switch SW2, the first terminal of the switch SW3, the first input terminal of the comparator CMP1, and the first input terminal of the comparator CMP2. In addition, the pad VOUT is connected to the signal line LS. When the communication mode is the first mode, the image data are output from the switch SW1 and are input to the pad VOUT. The image data are output to the signal line LS via the pad VOUT. When the communication mode is the second mode, the clock control signal or the negative voltage are input from the signal line LS to the pad VOUT. The negative voltage is output to the timing generator 104 and the pad VLO2 via the pad VOUT and the switch SW2. The clock control signal is output to the timing generator 104 and the VCO 105 via the pad VOUT and the switch SW3.

The pad VLO2 is connected to the second terminal of the switch SW2 and the capacitance element C1. When the communication mode is the second mode and the switch SW2 is in the ON state, the negative voltage is input to the pad VLO2. The negative voltage is output to the capacitance element C1 via the pad VLO2. The capacitance element C1 (voltage supply circuit) is connected to the pad VLO1 and the pad VLO2. When the communication mode is the second mode, the capacitance element C1 is electrically connected to the signal line LS. The capacitance element C1 holds the negative voltage and supplies the negative voltage to the imager 11.

The pad SYNC2 is connected to the timing generator 104 and the pad SYNC1. When the communication mode is the second mode, the control signal generated by the timing generator 104 is input to the pad SYNC2. The control signal is output to the imager 11 via the pad SYNC2.

The pad CLK2 is connected to the VCO 105 and the pad CLK1. The camera clock generated by the VCO 105 is input to the pad CLK2 and the timing generator 104 regardless of the communication mode. The camera clock is output to the imager 11 via the pad CLK2.

The camera unit 10 and the processor 6 are connected to each other by the signal line LS, the power source line LV (first power source line), and the ground line LG (second power source line). The power source line LV transmits, from the processor 6 to the camera unit 10, the power source voltage that is to be supplied to the imager 11. The ground line LG transmits, front the processor 6 to the camera unit 10, the ground voltage that is to be supplied to the imager 11. The voltage transmitted by the ground line LG has only to be the substrate voltage lower than the power source voltage and higher than the negative voltage described above.

The camera unit 10 includes three types of pads. The first pad (pad VOUT) of the camera unit 10 is electrically connected to the signal line LS. The second pad (pad VDD1 and pad VDD2) of the camera unit 10 is electrically connected to the power source line LV. The third pad (pad GND1 and pad GND2) of the camera unit 10 is electrically connected to the ground line LG. The camera unit 10 is electrically connected to the processor 6 via only the first pad, the second pad, and the third pad. Other than the above-described three types of pads, no pads electrically connecting the camera unit 10 and the processor 6 together are disposed in the camera unit 10.

When the communication mode is the first mode, the image reception circuit 60 receives the image data transmitted by the camera unit 10. When the communication mode is the second mode, the signal output circuit 61 outputs the clock control signal or the negative voltage to the signal line LS. The image reception circuit 60 and the signal output circuit 61 operate on the basis of the system clock of the processor 6.

Figure 3:
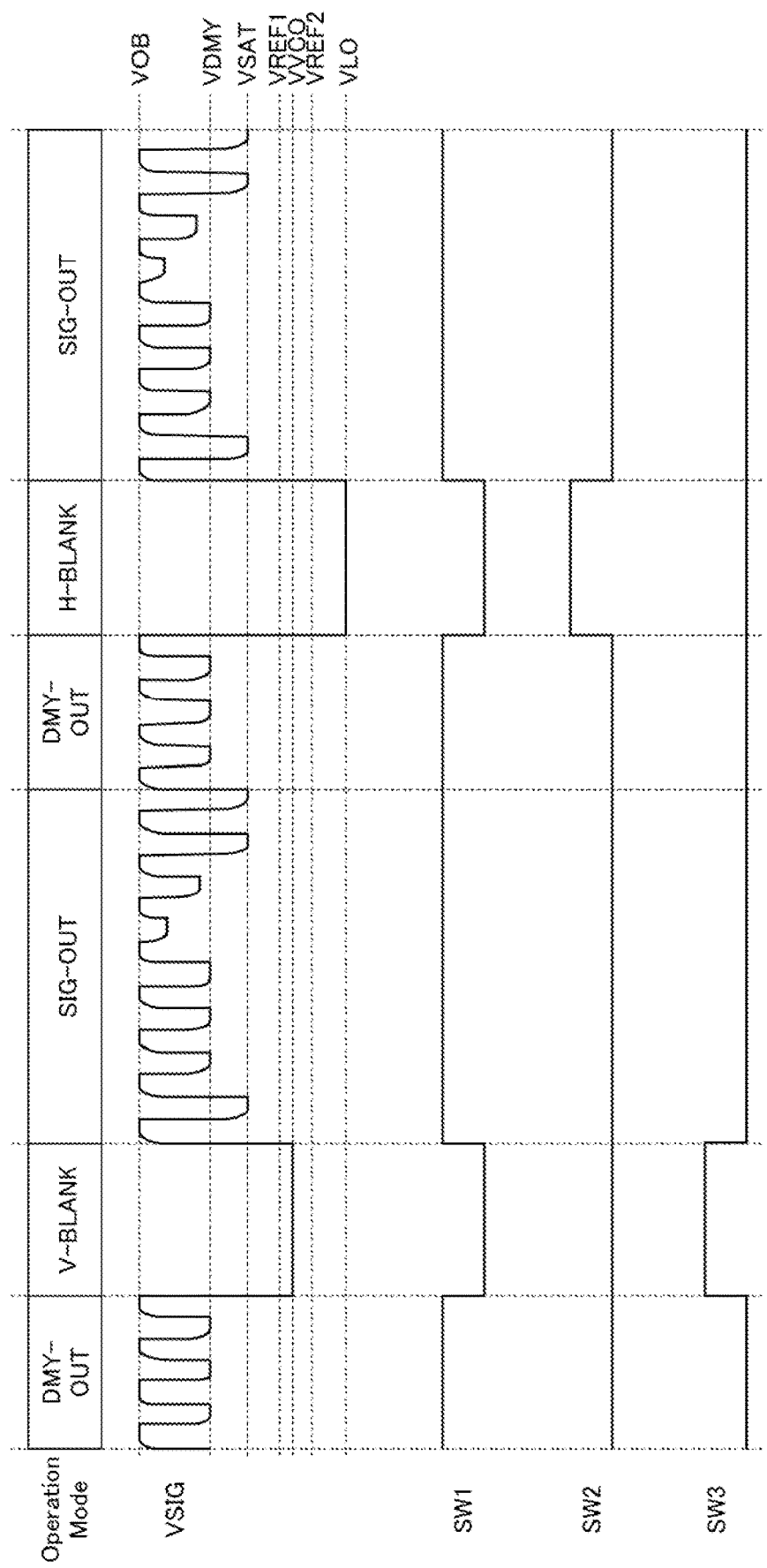
FIG. 3 is a timing chart of communication in the endoscope system according to the first embodiment of the present invention.
Figure 4:
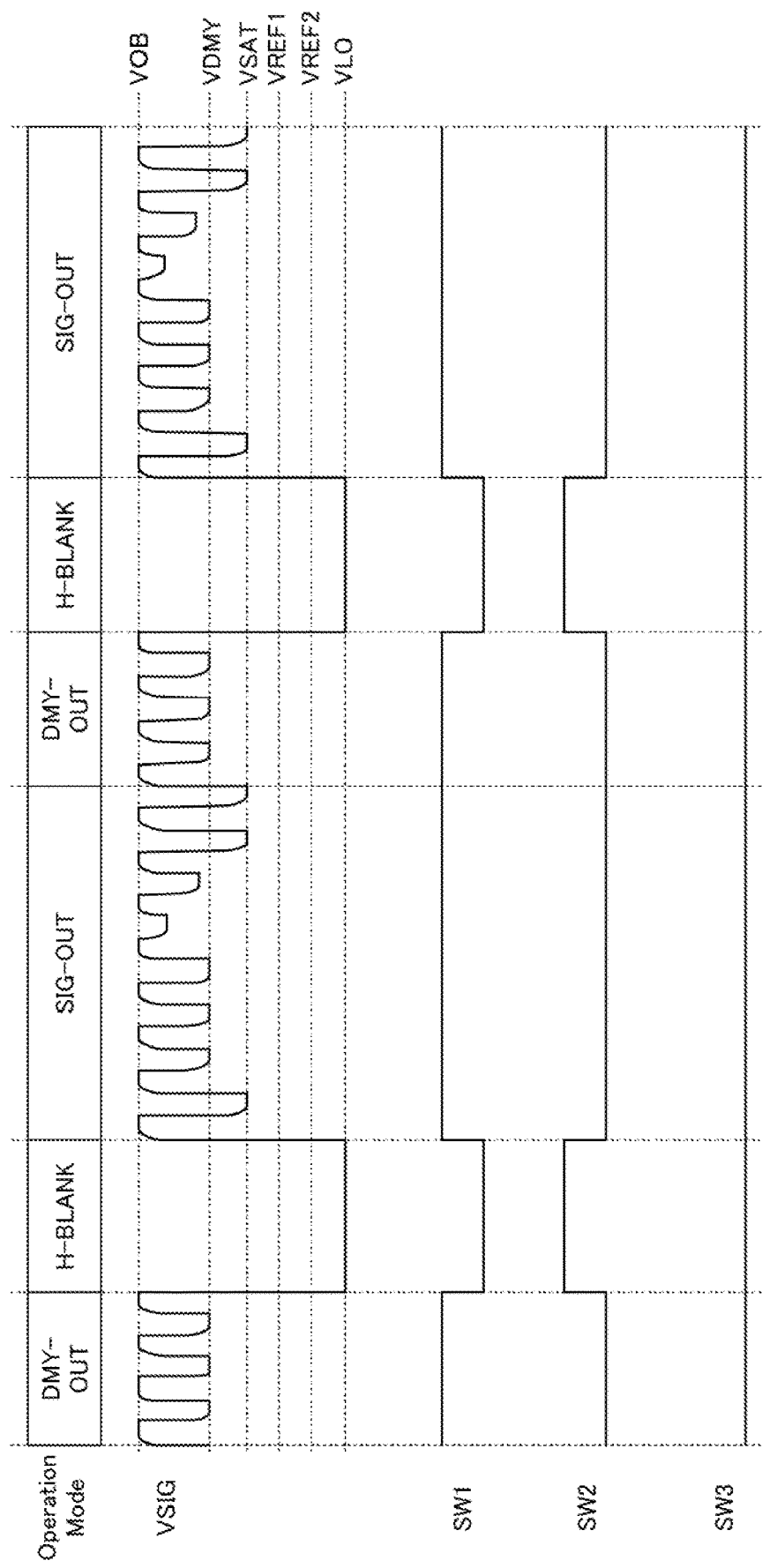
FIG. 4 is a timing chart of communication in the endoscope system according to the first embodiment of the present invention.

FIG. 3 and FIG. 4 show timings of communication in the endoscope system 1. Time passes in the right direction in FIG. 3 and FIG. 4. The operation mode of the imager 11, the electric potential (VSIG) of the signal line LS, the state of the switch SW1, the state of the switch SW2, and the state of the switch SW3 are shown in FIG. 3 and FIG. 4.

An operation in an image-output period (SIG-OUT) will be described. In the image-output period, the communication mode is the first mode. When the image-output period is started, the controller CTL sets the state of the switch SW1 to the ON state and sets the state of each of the switch SW2 and the switch SW3 to the OFF state. The buffer 102 is electrically connected to the signal line LS. The image data generated by the imager 11 are output to the signal line LS via the buffer 101, the buffer 102, and the switch SW1. The image reception circuit 60 receives the image data.

The maximum value of the signal level of the image data output to the signal line LS is VOB. The minimum value of the signal level of the image data output to the signal line LS is VSAT. The range of the signal level of the image data output to the signal line LS is greater than or equal to VSAT and less than or equal to VOB.

An electric potential VREF1 and an electric potential VREF2 are shown. The electric potential VREF1 is an electric potential input to the second input terminal of the comparator CMP1. The electric potential VREF2 is an electric potential input to the second input terminal of the comparator CMP2. The electric potential VREF1 is lower than the electric potential VSAT. The electric potential VREF2 is lower than the electric potential VREF1. When the signal line LS is transmitting the image data, the electric potential of the signal line LS is higher than the electric potential VREF1 and is higher than the electric potential VREF2. Therefore, the controller CTL maintains the state of the switch SW1 to be the ON state and maintains the state of each of the switch SW2 and the switch SW3 to be the OFF state in order to transmit the image data.

An operation in a dummy-output period (DMY-OUT) will be described. In the dummy output period, the communication mode is the first mode. The imager 11 outputs dummy data in the dummy-output period. The dummy data are output to the signal line LS via the buffer 101, the buffer 102, and the switch SW1. The image reception circuit 60 receives the dummy data. The dummy data are used in the processor 6 for adjusting the system clock of the processor 6.

The maximum value of the signal level of the dummy data output to the signal line LS is VOB. The minimum value of the signal level of the dummy data output to the signal line LS is VDMY. The electric potential VDMY is greater than or equal to the electric potential VSAT. The range of the signal level of the dummy data output to the signal line LS is greater than or equal to VDMY and less than or equal to VOB.

When the signal line LS is transmitting the dummy data, the electric potential of the signal line LS is higher than the electric potential VREF1 and is higher than the electric potential VREF2. Therefore, the controller CTL maintains the state of the switch SW1 to be the ON state and maintains the state of each of the switch SW2 and the switch SW3 to be the OFF state in order to transmit the dummy data.

The imager 11 stops outputting the image data and the dummy data in a blanking period. A plurality of blanking periods of the imager 11 include a vertical blanking period and a horizontal blanking period. The vertical blanking period is arranged between a timing at which reading of the image data of one frame is completed and a liming at which reading of the image data of next one frame is started. The horizontal blanking period is arranged between a timing at which reading of the image data of one row in one frame is completed and a timing at which reading of the image data of next one row in the frame is started. The image data of one frame include image data of multiple rows. After the operation shown in FIG. 3 is executed, the operation shown in FIG. 4 is executed.

An operation in the vertical blanking period (V-BLANK) will be described. The signal output circuit 61 outputs the clock control signal having a predetermined electric potential (VVCO) to the signal line LS at a predetermined timing in the dummy output period. When the signal line LS is transmitting the clock control signal, the electric potential of the signal line LS is higher than the electric potential VREF2 and is lower than the electric potential VREF1. Therefore, the controller CTL determines that the signal line LS is transmitting the clock control signal. The controller CTL sets the state of the switch SW1 to the OFF state and sets the state of the switch SW3 to the ON state. The controller CTL maintains the state of the switch SW2 to be the OFF state. At this time, the communication modes are switched from the first mode to the second mode and the vertical blanking period is started.

Since the state of the switch SW1 changes to the OFF state, the output of the dummy data to the signal line LS is stopped. Since the state of the switch SW3 changes to the ON state, the clock control signal transmitted by the signal line LS is input to the timing generator 104 and the VCO 105.

The timing generator 104 starts execution of counting on the basis of the clock control signal. The VCO 105 tunes the frequency of the camera clock to a frequency corresponding to the voltage of the clock control signal. Accordingly, in the first embodiment, the signal output circuit 61 can switch the communication modes from the first mode to the second mode and can execute a tuning operation of the frequency of the camera clock on the basis of the clock control signal by transmitting the clock control signal having the electric potential (VVCO) that is not included in the range of the signal level of the image data to the signal line LS.

When a predetermined clock number is counted, the timing generator 104 outputs a control signal for starting reading (frame reading) of the pixel signal in the imager 11 to the imager 11. At this time, the timing generator 104 outputs a control signal for switching the communication modes to the controller CTL. The controller CTL sets the state of the switch SW1 to the ON state and sets the state of the switch SW3 to the OFF state on the basis of the control signal output from the timing generator 104. The controller CTL maintains the state of the switch SW2 to be the OFF state. At this time, the communication modes are switched from the second mode to the first mode and the image-output period is started. In the image-output period, the operation described above is executed.

An operation in the horizontal blanking period (H-BLANK) will be described. The signal output circuit 61 outputs a negative voltage VLO to the signal line LS at a predetermined timing in the dummy-output period. For example, the negative voltage VLO is −0.9 V. When the signal line LS is transmitting the negative voltage VLO, the electric potential of the signal line LS is lower than the electric potential VREF2. Therefore, the controller CTL determines that the signal line LS is transmitting the negative voltage VLO. The controller CTL sets the state of the switch SW1 to the OFF state and sets the state of the switch SW2 to the ON state. The controller CTL maintains the state of the switch SW3 to be the OFF state. At this time, the communication modes are switched from the first mode to the second mode and the horizontal blanking period is started.

Since the state of the switch SW1 changes to the OFF state, the output of the dummy data to the signal line LS is stopped. Since the state of the switch SW2 changes to the ON state, the negative voltage VLO transmitted by the signal line LS is input to the timing generator 104 and the capacitance element C1.

The timing generator 104 starts execution of clock-counting on the basis of the negative voltage VLO. The capacitance element C1 outputs the negative voltage VLO to the imager 11.

In a 4-transistor-type CMOS imager, a dark current can be reduced by biasing a transfer gate (TG) to a negative electric potential in a signal accumulation period. The negative voltage VLO is supplied to a transfer gate in the imager 11.

When a predetermined clock number is counted, the timing generator 104 outputs a control signal for starting horizontal reading of the pixel signal in the imager 11 to the imager 11. At this time, the timing generator 104 outputs a control signal for switching the communication modes to the controller CTL. The controller CTL sets the state of the switch SW1 to the ON state and sets the state of the switch SW2 to the OFF state on the basis of the control signal output from the timing generator 104. The controller CTL maintains the state of the switch SW3 to be the OFF state. At this time, the communication modes are switched from the second mode to the first mode and the image-output period is started. In the image-output period, the operation described above is executed.

In the above-described description, the timing generator 104 outputs the control signal for switching the communication modes from the second mode to the first mode to the controller CTL. The timing generator 104 may output a control signal for controlling the state of each switch to each switch at a timing at which the communication modes are switched from the second mode to the first mode.

In the first embodiment, the signal output circuit 61 outputs the first electric potential (VVCO) to the signal line LS. The first electric potential corresponds to the signal level that is not included in the range of the signal level of the image data output to the signal line LS. When the controller CTL detects the first electric potential in the first mode, the controller CTL switches the communication modes from the first mode to the second mode. Since switching of the communication modes is controlled on the basis of the signal output from the processor 6, the endoscope system 1 can improve the accuracy of the operation of switching the communication modes.

The camera unit 10 is electrically connected to the processor 6 via only the first pad, the second pad, and the third pad. Therefore, the transmission cable 3 can be thinned.

The signal output circuit 61 outputs the negative voltage VLO to the signal line LS in the horizontal blanking period of the imager 11 and outputs the clock control signal to the signal line LS in the vertical blanking period of the imager 11. Therefore, a dark current can be reduced in a signal accumulation period of pixels of each row in the pixel unit 100. Since the negative voltage VLO is supplied from the processor 6, the camera unit 10 does not need to include a voltage generation circuit that generates the negative voltage VLO. Therefore, the camera unit 10 can be miniaturized.

Modified Example of First Embodiment

A modified example of the first embodiment will be described. A method of switching the communication modes from the second mode to the first mode is different from that described in the first embodiment.

After the signal output circuit 61 outputs the first electric potential to the signal line LS, the signal output circuit 61 outputs a second electric potential to the signal line LS. The second electric potential corresponds to the signal level included in the range of the signal level of the image data output to the signal line LS. When the controller CTL detects the second electric potential in the second mode, the controller CTL switches the communication modes front the second mode to the first mode.

As long as the second electric potential falls within the range from the minimum value of the signal level of the image data to the maximum value of the signal level of the image data, the second electric potential may be any electric potential.

Second Embodiment

Figure 5:
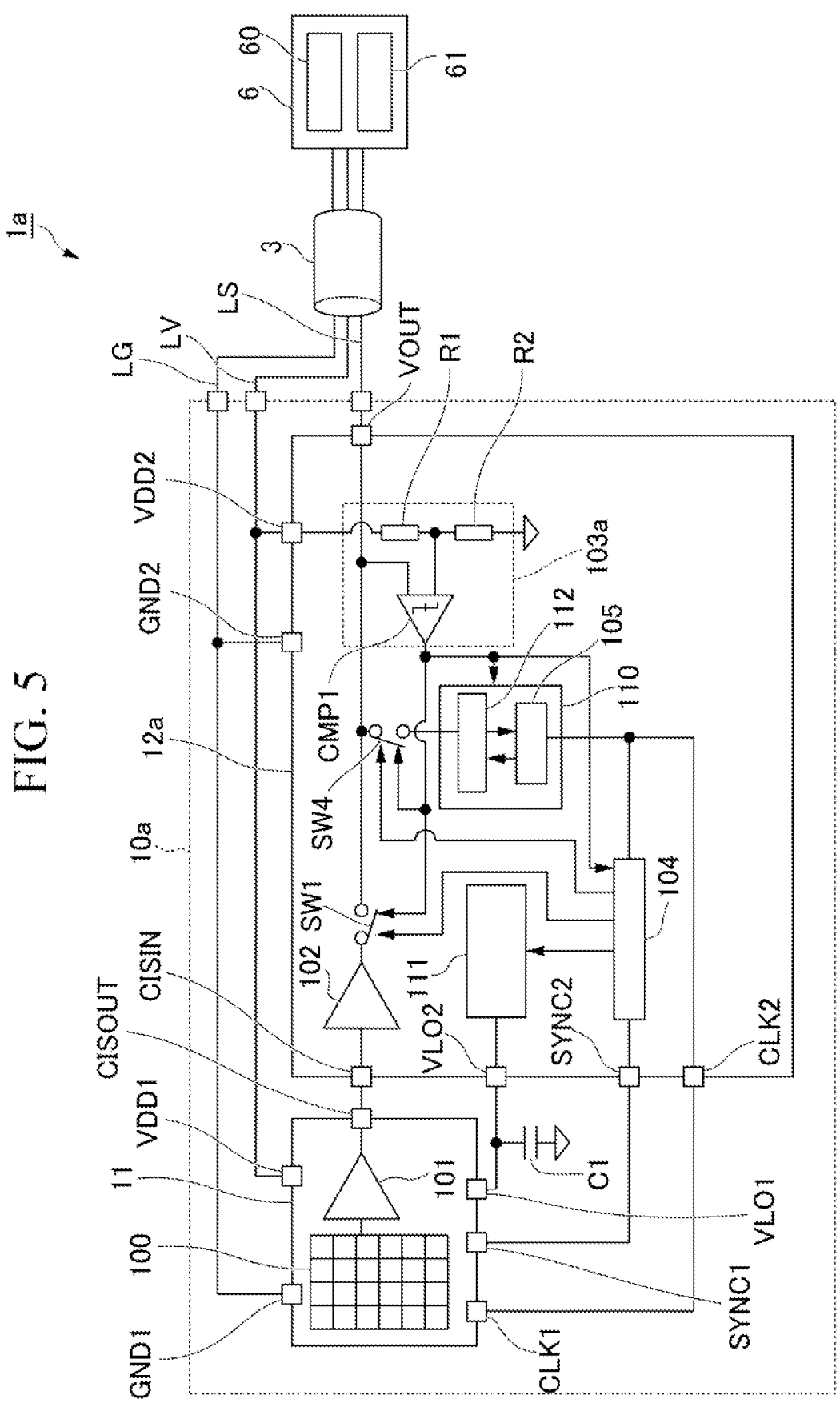
FIG. 5 is a block diagram showing a configuration of an endoscope system according to a second embodiment of the present invention.

FIG. 5 shows an internal configuration of an endoscope system 1a according to a second embodiment of the present invention. The same parts as those shown in FIG. 2 will not be described.

The endoscope system 1a includes a camera unit 10a and a processor 6. The camera unit 10a includes an imager 11 and a control unit 12a. The control unit 12a includes a buffer 102, a communication control circuit 103a, a timing generator 104, a phase-locked loop (PLL) 110 (clock adjustment circuit), a voltage generation circuit 111, a switch SW1, and a switch SW4.

The communication control circuit 103a includes a comparator CMP1, a resistor R1, and a resistor R2. Each of the resistor R1 and the resistor R2 includes a first terminal and a second terminal. The first terminal of the resistor R1 is connected to a power source line LV. The power source voltage is input to the first terminal of the resistor R1. The first terminal of the resistor R2 is connected to the second terminal of the resistor R1. The ground voltage is input to the second terminal of the resistor R2. The resistor R1 and the resistor R2 generate an electric potential that is based on the power source voltage, the ground voltage, and the resistance value of each resistor.

The comparator CMP1 includes a first input terminal, a second input terminal, and an output terminal. The first input terminal of the comparator CMP1 is connected to a signal line LS. The second input terminal of the comparator CMP1 is connected to the second terminal of the resistor R1. The output terminal of the comparator CMP1 is connected to the controller CTL, the PLL 110, the switch SW1, the switch SW4, and the timing generator 104.

The comparator CMP1 compares the electric potential of the signal line LS with a predetermined electric potential. The comparator CMP1 outputs a signal indicating the comparison results to the switch SW1, the switch SW4, the PLL 110, and the timing generator 104. The state of each of the switch SW1 and the switch SW4 is controlled on the basis of the signal output from the comparator CMP1 to each of the switch SW1 and the switch SW4. The comparator CMP1 switches the communication modes of the camera unit 10a between the first mode and the second mode.

In a case in which the buffer 101 is a source follower circuit including an NMOS transistor, the comparator CMP1 detects an electric potential higher than the maximum value of the signal level of the image data output to the signal line LS. In a case in which the buffer 101 is a source follower circuit including a PMOS transistor, the comparator CMP1 detects an electric potential lower than the minimum value of the signal level of the image data output to the signal line LS.

The switch SW4 includes a first terminal and a second terminal. The state of the switch SW4 becomes any one of the ON state and the OFF state. When the state of the switch SW4 is the ON state, the first terminal and the second terminal are electrically connected to each other. When the state of the switch SW4 is the OFF state, the first terminal and the second terminal are electrically insulated from each other.

The first terminal of the switch SW4 is connected to the signal line LS and the second terminal of the switch SW4 is connected to the PLL 110. When the communication mode is the second mode, the state of the switch SW4 becomes the ON state. At this time, a clock control signal is output from the signal line LS to the PLL 110. The switch SW4 receives the clock control signal from the processor 6. When the communication mode is the first mode, the state of the switch SW4 becomes the OFF state.

The PLL 110 includes a VCO 105 and a clock control circuit 112. The clock control circuit 112 includes a phase comparator, a charge pump, and a loop filter. The PLL 110 switches operations on the basis of the signal output from the comparator CMP1. The signal output from the comparator CMP1 indicates the communication mode. When the communication mode is the second mode, the PLL 110 executes an operation for synchronizing the camera clock with the system clock of the processor 6. When the communication mode is the first mode, the PLL 110 stops the operation for synchronizing the camera clock with the system clock of the processor 6 and continues to output a clock while the clock frequency at the moment at which the communication mode is shifted from the second mode to the first mode is maintained.

The clock control circuit 112 is connected to the second terminal of the switch SW4. When the communication mode is the second mode, the clock control signal is input to the clock control circuit 112. The clock control signal in the second embodiment is a pulse signal having a cycle that is integer times longer than the cycle of the system clock of the processor 6. The clock control circuit 112 outputs a voltage corresponding to the frequency to the VCO 105. The clock control signal has a first electric potential that is not included in a range of a signal level of the image data output to the signal line LS.

The VCO 105 generates the camera clock having a frequency corresponding to the voltage output front the clock control circuit 112. In this way, the VCO 105 synchronizes the camera clock with the pulse signal (clock control signal). The VCO 105 outputs the generated camera clock to the timing generator 104 and the imager 11. When the communication mode is the second mode, the VCO 105 adjusts the frequency of the camera clock. When the communication mode is the first mode, the VCO 105 generates the camera clock having a frequency that has been set in the second mode.

When the signal indicating the second mode is output from the comparator CMP1 and is input to the timing generator 104, the timing generator 104 starts execution of clock-counting. The timing generator 104 executes counting on the basis of the camera clock output from the VCO 105. The timing generator 104 outputs a control signal for controlling reading of the pixel signal in the imager 11 to the imager 11 on the basis of the counted value. In addition, when a predetermined number is counted, the timing generator 104 outputs a control signal for switching the communication modes from the second mode to the first mode to the switch SW1 and the switch SW4. In addition, when the communication mode is the second mode, the timing generator 104 outputs a control signal for causing the voltage generation circuit 111 to generate a negative voltage to the voltage generation circuit 111.

The voltage generation circuit 111 is connected to the pad VLO2. The voltage generation circuit 111 generates the negative voltage in a horizontal blanking period and outputs the negative voltage to the capacitance element C1. The capacitance element C1 outputs the negative voltage to the imager 11.

Figure 6:
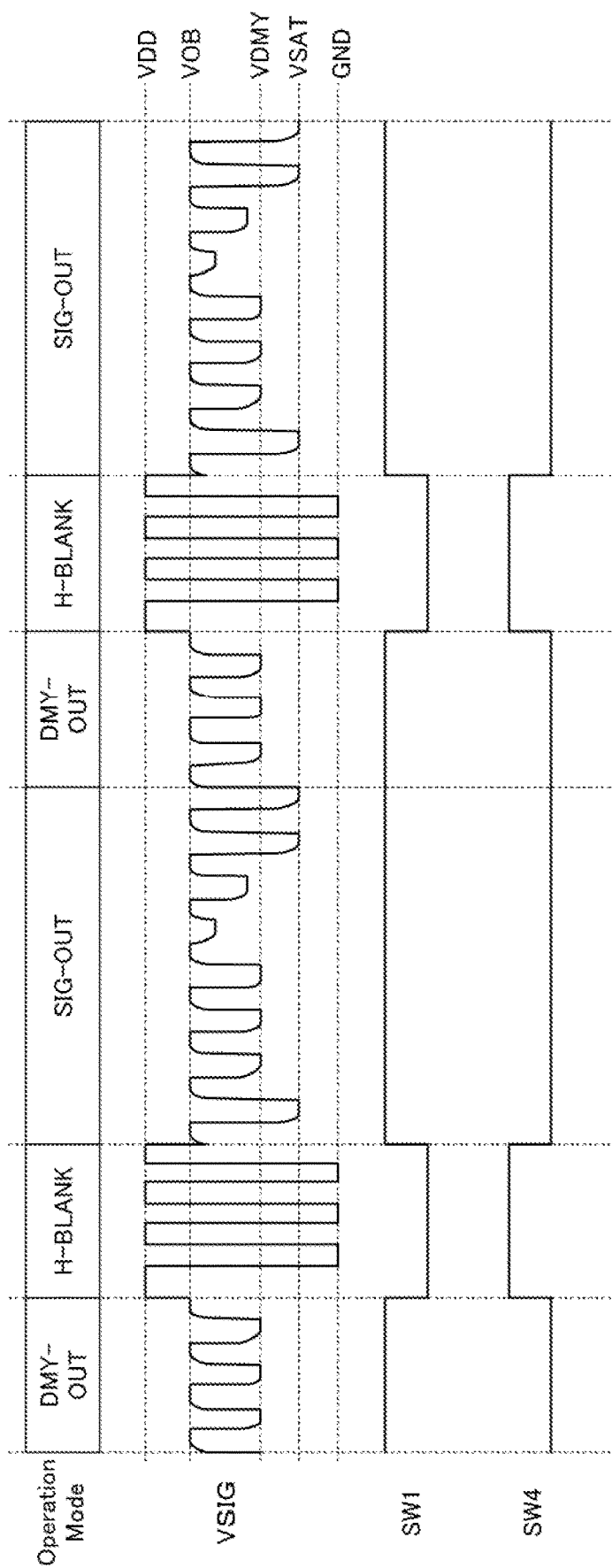
FIG. 6 is a timing chart of communication in the endoscope system according to the second embodiment of the present invention.

FIG. 6 shows timings of communication in the endoscope system 1*a*. Time passes in the right direction in FIG. 6. The operation mode of the imager 11, the electric potential (VSIG) of the signal line LS, the state of the switch SW1, and the state of the switch SW4 are shown in FIG. 6. Hereinafter, an operation in a case in which the buffer 101 is a source follower circuit including an NMOS transistor will be described.

An operation in an image-output period (SIG-OUT) will be described. In the image-output period, the communication mode is the first mode. When the image-output period is started, the state of the switch SW1 becomes the ON state and the state of the switch SW4 becomes the OFF state. The buffer 102 is electrically connected to the signal line LS. The image data generated by the imager 11 are output to the signal line LS via the buffer 101, the butter 102, and the switch SW1. The image reception circuit 60 receives the image data.

The maximum value of the signal level of the image data output to the signal line LS is VOB. The minimum value of the signal level of the image data output to the signal line LS is VSAT. The range of the signal level of the image data output to the signal fine LS is greater than or equal to VSAT and less than or equal to VOB.

The electric potential of the second terminal of the resistor R1, that is, the electric potential of the second input terminal of the comparator CMP1 is higher than the electric potential VOB. When the signal line LS is transmitting the image data, the electric potential of the signal line LS is less than or equal to the electric potential VOB. The comparator CMP1 outputs a signal indicating the comparison results to the switch SW1 and the switch SW4. The state of the switch SW1 is maintained to be the ON state and the state of the switch SW4 is maintained to be the OFF state.

An operation in a dummy-output period (DMY-OUT) will be described. In the dummy-output period, the communication mode is the first mode. The imager 11 outputs dummy data in the dummy-output period. The dummy data are output to the signal line LS via the buffer 101, the buffer 102, and the switch SW1. The image reception circuit 60 receives the dummy data.

The maximum value of the signal level of the dummy data output to the signal line LS is VOB. The minimum value of the signal level of the dummy data output to the signal line LS is VDMY. The electric potential VDMY is higher than the electric potential VSAT. The range of the signal level of the dummy data output to the signal line LS is greater than or equal to VDMY and less than or equal to VOB.

When the signal line LS is transmitting the dummy data, the electric potential of the signal line LS is less than or equal to the electric potential VOB and is greater than or equal to the electric potential VSAT. The comparator CMP1 outputs a signal indicating the comparison results to the switch SW1 and the switch SW4. The state of the switch SW1 is maintained to be the ON state and the state of the switch SW4 is maintained to be the OFF state.

An operation in a horizontal blanking period (H-BLANK) will be described. The signal output circuit 61 outputs the clock control signal to the signal line LS at a predetermined timing in the dummy-output period. The maximum value of the signal level of the clock control signal output to live signal line LS is a power source voltage VDD. The power source voltage VDD is higher than the electric potential VOB. The minimum value of the signal level of the clock control signal output to the signal line LS is a ground voltage GND. The ground voltage GND is lower than the electric potential VSAT.

When the clock control signal is output to the signal line LS, the electric potential of the signal line LS is higher than the electric potential VOB. The comparator CMP1 outputs a signal indicating the comparison results to the switch SW1 and the switch SW4. The state of the switch SW1 is set to the OFF state and the state of the switch SW4 is set to the ON state. At this time, the communication modes are switched from the first mode to the second mode and the horizontal blanking period is started.

Since the state of the switch SW1 changes to the OFF state, the output of the dummy data to the signal line LS is stopped. Since the state of the switch SW4 changes to the ON state, the clock control signal transmitted by the signal line LS is input to the PLL 110. The clock control circuit 112 of the PLL 110 outputs the voltage corresponding to the frequency of the clock control signal to the VCO 105.

The VCO 105 generates the camera clock having a frequency corresponding to the voltage output from the clock control circuit 112. The VCO 105 outputs the generated camera clock to the timing generator 104 and the imager 11.

When the horizontal blanking period is started, the timing generator 104 outputs a control signal for causing the voltage generation circuit 111 to generate the negative voltage to the voltage generation circuit 111. The voltage generation circuit 111 generates the negative voltage and outputs the negative voltage to the capacitance element C1. The capacitance element C1 outputs the negative voltage to the imager 11.

When the horizontal blanking period is started, the timing generator 104 starts execution of counting. When a predetermined number is counted, the timing generator 104 outputs a control signal for starting reading of the pixel signal in the imager 11 to the imager 11. At this time, the timing generator 104 outputs a control signal for switching the communication modes to the switch SW1 and the switch SW4. The state of the switch SW1 is set to the ON state and the state of the switch SW4 is set to the OFF state. At this time, the communication modes are switched from the second mode to the first mode and the image-output period is started. In the image-output period, the operation described above is executed.

The operation in the vertical blanking period is similar to that in the horizontal blanking period.

In the above-described operation, the comparator CMP1 detects the electric potential of the signal line LS higher than the electric potential VOB and switches the communication modes from the first mode to the second mode in the dummy-output period. In a case in which the buffer 101 is a source follower circuit including a PMOS transistor, the comparator CMP1 detects the electric potential of the signal line LS lower than the electric potential VSAT and switches the communication modes from the first mode to the second mode in the dummy-output period.

In the second embodiment, the signal output circuit 61 outputs the first electric potential (VDD) to the signal line LS. The first electric potential corresponds to the signal level that is not included in the range of the signal level of the image data output to the signal line LS. When the comparator CMP1 detects the first electric potential in the first mode, the comparator CMP1 switches the communication modes from the first mode to the second mode. Since switching of the communication modes is controlled on the basis of the signal output from the processor 6, the endoscope system 1a can improve the accuracy of the operation of switching the communication modes.

In the first embodiment, an analog voltage for controlling the VCO 105 is transmitted to the camera unit 10 via the transmission cable 3 as the clock control signal. The endoscope system 1a according to the second embodiment is unlikely to be influenced by noise generated through driving an electric scalpel or the like, compared to the endoscope system 1 according to the first embodiment.

Third Embodiment

Figure 7:
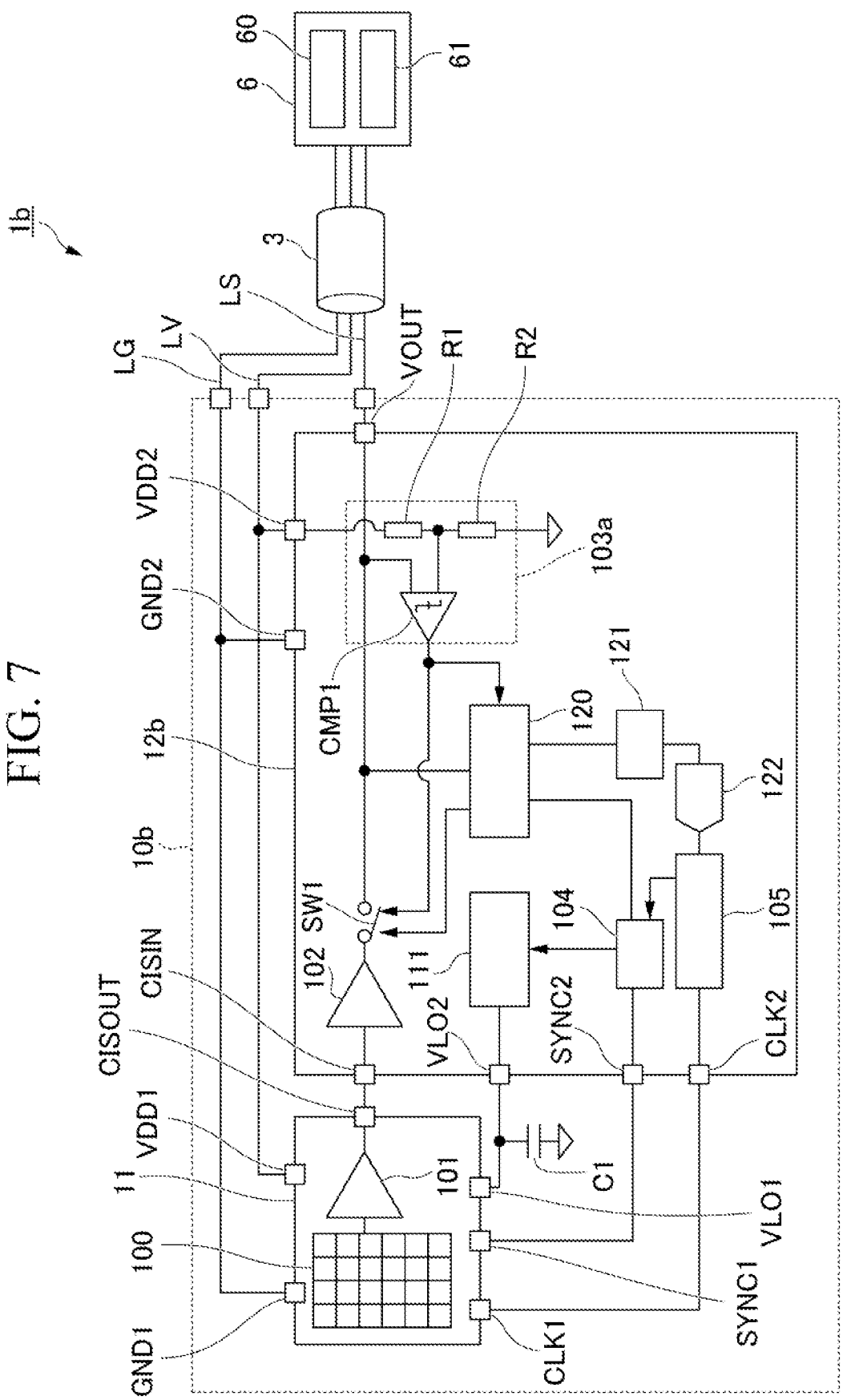
FIG. 7 is a block diagram showing a configuration of an endoscope system according to a third embodiment of the present invention.

FIG. 7 shows an internal configuration of an endoscope system 1b according to a third embodiment of the present invention. The same parts as those shown in FIG. 5 will not be described. The endoscope system 1b includes a camera unit 10b and a processor 6. The camera unit 10b includes an imager 11 and a control unit 12b. The control unit 12b includes a buffer 102, a communication control circuit 103a, a tinting generator 104, a VCO 105, a voltage generation circuit 111, a clock-data recovery (CDR) circuit 120, a resistor circuit 121, a digital-to-analog converter (DAC) circuit 122, and a switch SW1.

The clock control signal in the third embodiment is a digital signal indicating a value corresponding to the frequency of the system clock of the processor 6. The clock control signal includes data (control data) indicating a value of the frequency. The clock control signal has a first electric potential corresponding to a signal level that is not included in a range of a signal level of image data output to a signal line LS. The CDR circuit 120 extracts the control data from the clock control signal. The resistor circuit 121 holds the control data. The DAC circuit 122 and the VCO 105 constitute a clock adjustment circuit. The DAC circuit 122 generates an analog signal having a voltage corresponding to the control data. The VCO 105 generates a camera clock having a frequency corresponding to the voltage of the analog signal.

Figure 8:
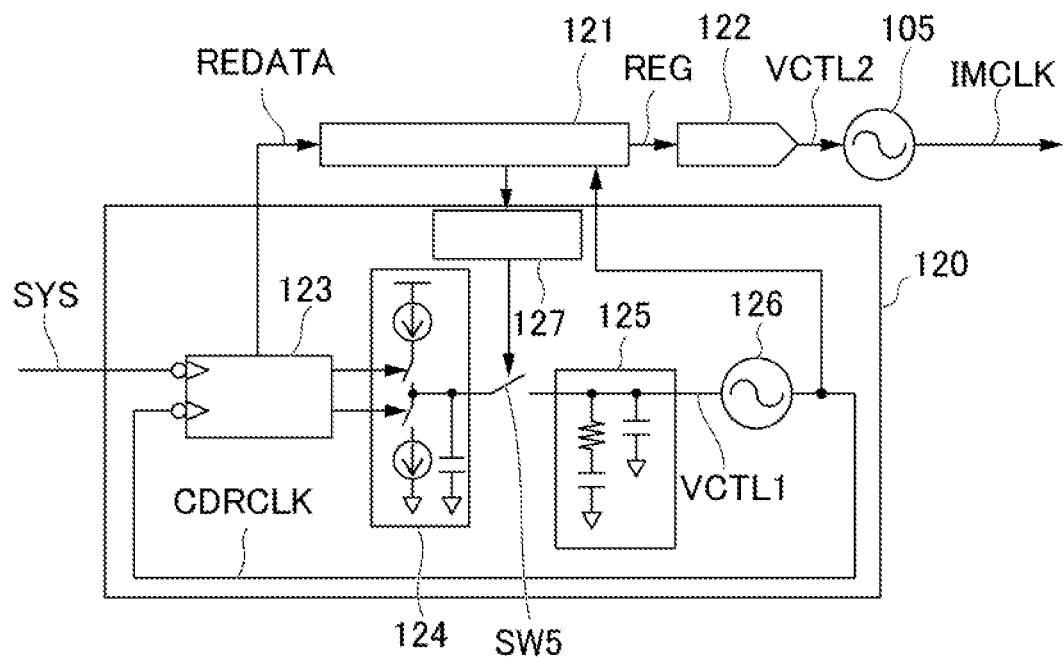
FIG. 8 is a block diagram showing a configuration of a CDR circuit included in the endoscope system according to the third embodiment of the present invention.

FIG. 8 shows a configuration of the CDR circuit 120. The CDR circuit 120 shown in FIG. 8 includes a phase-frequency comparator 123, a charge pump 124, a loop filter 125, a VCO 126, a communication control circuit 127, and a switch SW5.

The CDR circuit 120 is connected to a pad VOUT. A clock control signal SYS output from a signal output circuit 61 and a CDR clock CDRCLK generated by the VCO 126 are input to the phase-frequency comparator 123. The clock control signal SYS includes a clock recovery symbol for each predetermined cycle. The clock recovery symbol includes a clock edge for detecting a transition timing of data. As data including the clock recovery symbol, for example, data of the format such as 8b/10b conversion, Manchester encoding, or the like may be used. In a case in which a cycle (the shortest cycle of the input clock) of data of one bit is defined as T, at least one clock recovery symbol (clock shift) is included in 5 T in the case of 8b/10b conversion and at least one clock recovery symbol (clock shift) is included in 2 T in the case of Manchester encoding.

When the communication mode is the second mode, the CDR circuit 120 adjusts a frequency of a camera clock IMCLK. When the communication mode is the first mode, the CDR circuit 120 generates the camera clock IMCLK having a frequency that has been set in the second mode. The CDR circuit 120 adjusts the phase and the frequency of the CDR clock CDRCLK so that a timing at which the clock control signal SYS falls and a timing at which the CDR clock CDRCLK falls match each other.

The phase-frequency comparator 123 samples a value of the clock control signal SYS at a timing of a rising edge of the CDR clock CDRCLK. The phase-frequency comparator 123 outputs control data REDATA synchronized with the camera clock IMCLK to the resistor circuit 121. In addition, the phase-frequency comparator 123 outputs a signal in accordance with the shift of the phase and the shift of the frequency between the clock control signal SYS and the CDR clock CDRCLK to the charge pump 124. The charge pump 124 generates an analog signal for adjusting the frequency of the CDR clock CDRCLK on the basis of the signal output from the phase-frequency comparator 123.

The switch SW5 is disposed between the charge pump 124 and the loop filter 125. When the communication modes are switched from the first mode to the second mode, the state of the switch SW5 becomes the ON state on the basis of the signal output from the communication control circuit 127. The loop filler 125 outputs, to the VCO 126, a control voltage VCTL1 that is based on the analog signal output from the charge pump 124. The VCO 126 generates the CDR clock CDRCLK having a frequency corresponding to the control voltage VCTL1. The VCO 126 outputs the CDR clock CDRCLK to the resistor circuit 121 and the phase frequency comparator 123. When the communication modes are switched from the second mode to the first mode, the state of the switch SW5 becomes the OFF state on the basis of the signal output from the communication control circuit 127. The voltage at the moment at which the communication modes are switched from the second mode to the first mode is maintained as the control voltage VCTL1 output by the loop filter 125. The oscillation frequency of the VCO 126 is fixed in a period during which the communication mode is the first mode.

The control data REDATA output from the phase-frequency comparator 123 is input to the resistor circuit 121 in synchronization with the CDR clock CDRCLK. The digital value of the control data REDATA is stored on the resistor circuit 121.

The digital value REG of the control data REDATA is read from the resistor circuit 121 and is output to the DAC circuit 122. The DAC circuit 122 generates a control voltage VCTL2 corresponding to the digital value REG and outputs the control voltage VCTL2 to the VCO 105. The VCO 105 generates the camera clock IMCLK having a frequency corresponding to the control voltage VCTL2. The VCO 105 outputs the generated camera clock IMCLK to the timing generator 104 and the imager 11.

The communication control circuit 127 detects a predetermined value from the digital value of the control data REDATA stored on lire resistor circuit 121. When the predetermined value is detected, the communication control circuit 127 switches the communication modes from the second mode to the first mode.

An operation of the endoscope system 1b will be described. The operation of the endoscope system 1b is similar to that of the endoscope system 1a according to the second embodiment except for the operation related to switching of the communication modes. In the description below, the electric potential shown in FIG. 6 is referred to accordingly.

Regarding the operation in an image-output period (SIG-OUT) and a dummy-output period (DMY-OUT), the part different from the operation in the second embodiment will be described. When the communication mode is the first mode, the state of the switch SW5 is the OFF state. The loop filter 125 outputs the constant control voltage VCTL1 to the VCO 126. The frequency of the CDR clock CDRLK is maintained to be a constant value. A circuit of the processor 6 not shown in the drawing detects the frequency of the camera clock IMCLK of the camera unit 10 on the basis of the transition liming of the image data in the dummy-output period.

Regarding the operation in a horizontal blanking period (H-BLANK), the part different from the operation in the second embodiment will be described. The signal output circuit 61 outputs the clock control signal to the signal line LS at a predetermined timing in the dummy-output period. The clock control signal includes control data for adjusting the frequency of the camera clock IMCLK detected in the dummy-output period. When the clock control signal is output to the signal line LS, the electric potential of the signal line LS is higher than the electric potential VOB. The comparator CMP1 outputs a signal indicating the comparison results to the switch SW1 and the CDR circuit 120. The state of the switch SW1 is set to the OFF state. At this time, the communication modes are switched from the first mode to the second mode and the horizontal blanking period is started.

Since the state of the switch SW1 changes to the OFF state, the output of the dummy data to the signal line LS is stopped. The state of the switch SW5 becomes the ON state on the basis of the signal output from the comparator CMP1. The loop filter 125 outputs, to the VCO 126, the control voltage VCTL1 that is based on the analog signal output from the charge pump 124. The VCO 126 generates the CDR clock CDRCLK having a frequency corresponding to the control voltage VCTL1.

The control data REDATA are output from the phase-frequency comparator 123 and are stored on the resistor circuit 121. The DAC circuit 122 generates the control voltage VCTL2 corresponding to the digital value REG of the control data REDATA and outputs the control voltage VCTL2 to the VCO 105. The VCO 105 generates the camera clock IMCLK having a frequency corresponding to the control voltage VCTL2.

After the signal output circuit 61 outputs the first electric potential to the signal line LS, the signal output circuit 61 outputs a communication control signal indicating an instruction to switch the communication modes from the second mode to the first mode to the signal line LS. Specifically, the signal output circuit 61 outputs the clock control signal having a predetermined digital value to the signal line LS at a predetermined timing in the horizontal blanking period. The digital value indicates switching of the communication modes. For example, the digital value is 1011. The clock control signal having the digital value corresponds to the communication control signal.

The clock control signal in the third embodiment is a pulse signal indicating the system clock of the processor 6. The pulse signal includes a pattern of a high level and a low level. The pattern of the pulse signal corresponds to the data of the communication control signal.

Figure 9:
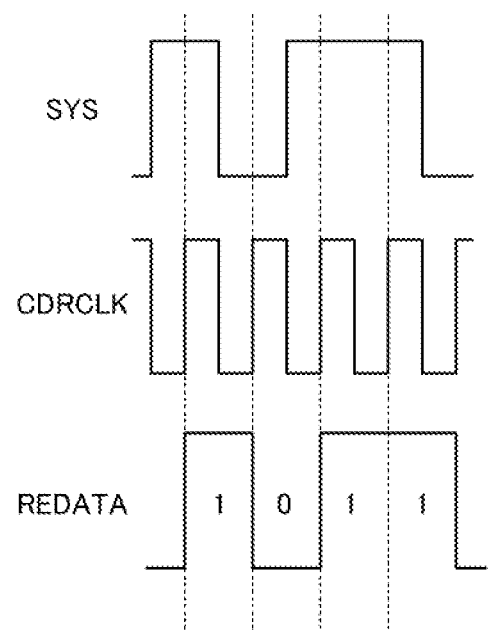
FIG. 9 is a timing chart showing waveforms of signals related to switching of communication modes in the third embodiment of the present invention.

FIG. 9 shows waveforms of signals related to switching of the communication modes. Time passes in the right direction in FIG. 9. The clock control signal SYS, the CDR clock CDRCLK, and the control data REDATA are shown in FIG. 9.

The phase-frequency comparator 123 samples a value of the clock control signal SYS at a timing of the rising edge of the CDR clock CDRCLK. The phase-frequency comparator 123 sequentially outputs the sampled values to the resistor circuit 121 as the control data REDATA. The control data REDATA are stored on the resistor circuit 121.

When the communication control circuit 127 detects the communication control signal in the second mode, the communication control circuit 127 switches the communication modes from the second mode to the first mode. Specifically, when it is determined that the digital value of the control data REDATA stored on the resistor circuit 121 is 1011, the communication control circuit 127 outputs a control signal to the switch SW5, the switch SW1, and the timing generator 104. At this time, the communication modes are switched from the second mode to the first mode and the image-output period is started. The state of the switch SW1 is set to the ON state and the state of the switch SW5 is set to the OFF state. The liming generator 104 outputs a control signal for starting reading of the pixel signal in the imager 11 to the imager 11.

In the third embodiment, the signal output circuit 61 outputs the first electric potential (VDD) to the signal line LS. The first electric potential corresponds to the signal level that is not included in the range of the signal level of the image data output to the signal line LS. When the comparator CMP1 defects the first electric potential in the first mode, the comparator CMP1 switches the communication modes from the first mode to the second mode. Since switching of the communication modes is controlled on the basis of the signal output from the processor 6, the endoscope system 1b can improve the accuracy of the operation of switching the communication modes.

In the first embodiment, an analog voltage for controlling the VCO 105 is transmitted to the camera unit 10 via the transmission cable 3 as the clock control signal. The endoscope system 1b according to the third embodiment is unlikely to be influenced by noise generated through driving an electric scalpel or the like, compared to the endoscope system 1 according to the first embodiment.

Fourth Embodiment

Figure 10:
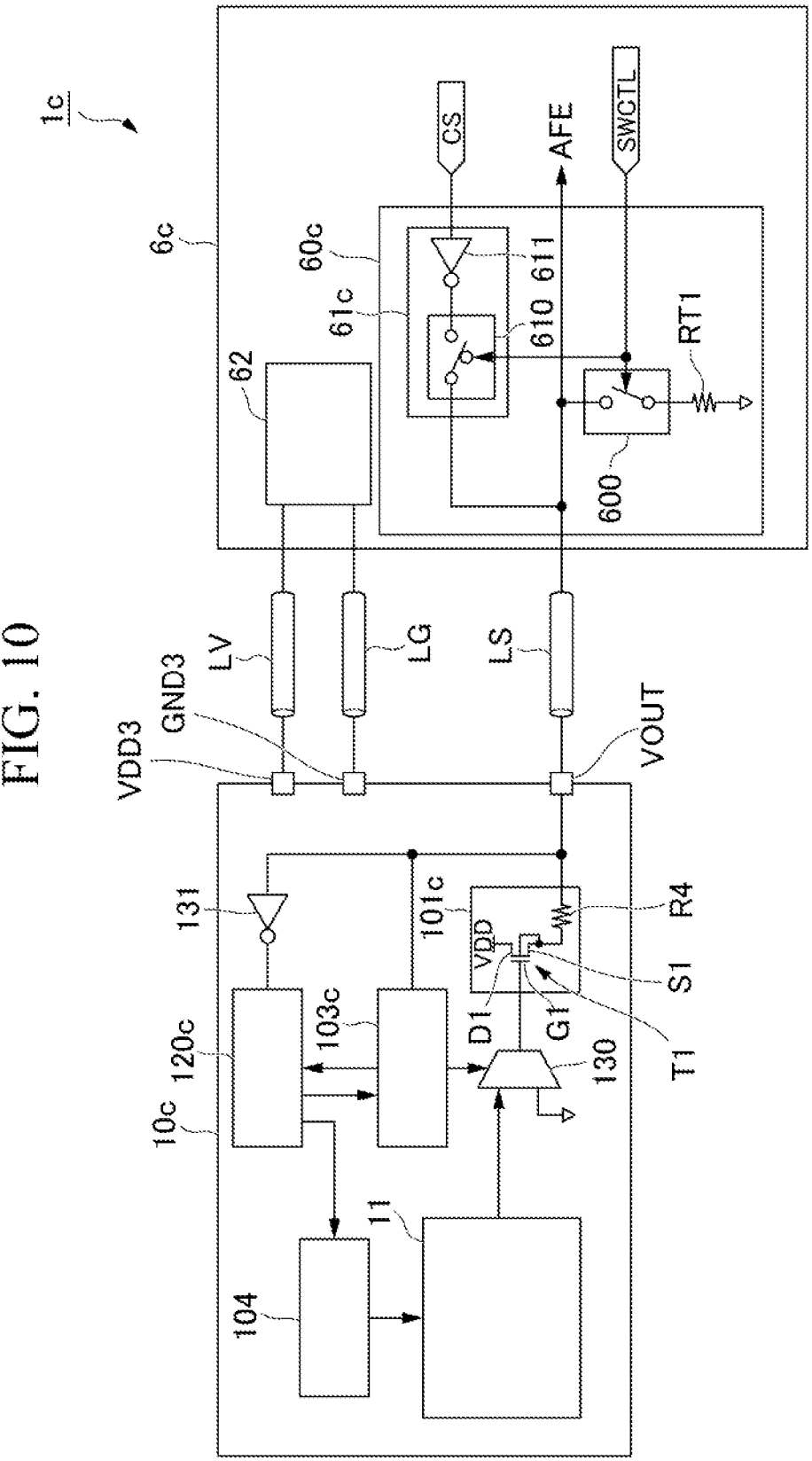
FIG. 10 is a block diagram showing a configuration of an endoscope system according to a fourth embodiment of the present invention.

FIG. 10 shows an internal configuration of an endoscope system 1c according to a fourth embodiment of the present invention. The same parts as those shown in FIG. 2 will not be described.

The endoscope system 1c includes a camera unit 10c and a processor 6c. The camera unit 10c includes an imager 11, a buffer 101c, a communication control circuit 103c, a timing generator 104, a CDR circuit 120c, a multiplexer 130, and an inverter 131.

The multiplexer 130 includes a first input terminal, a second input terminal, and an output terminal. The first input terminal of the multiplexer 130 is connected to the imager 11. Image data are input to the first input terminal of the multiplexer 130. The ground voltage is input to the second input terminal of the multiplexer 130. The multiplexer 130 outputs any one of the image data and the ground voltage to the buffer 101c.

The state of the multiplexer 130 is set to any one of a first state and a second state. When the communication mode is the first mode, the state of the multiplexer 130 is set to the first state. The multiplexer 130 outputs the image data to the buffer 101c. When the communication mode is the second mode, the state of the multiplexer 130 is set to the second state. The multiplexer 130 outputs the ground voltage to the buffer 101c.

The buffer 101c includes a transistor T1 and a resistor R4. The buffer 101c is a source follower circuit.

The transistor T1 includes a gate terminal G1 (first terminal), a drain terminal D1 (second terminal), and a source terminal S1 (third terminal). The gate terminal G1 is connected to the output terminal of the multiplexer 130. The image data or the ground voltage (substrate voltage) is input to the gate terminal G1. The power source voltage VDD is input to the drain terminal D1.

When the communication mode is the first mode, the image data are input to the gate terminal G1. The source terminal S1 outputs a third electric potential corresponding to a signal level of the image data to a signal line LS via the resistor R4. The maximum value of the third electric potential is less than or equal to a voltage lower than the power source voltage VDD by the threshold voltage of the transistor T1. The minimum value of the third electric potential is greater than or equal to the ground voltage (substrate voltage).

When the communication mode is the second mode, the ground voltage is input to the gate terminal G1. The state of the transistor T1 becomes the OFF state. Therefore, the output of the image data to the signal line LS is stopped.

The resistor R4 includes a first terminal and a second terminal. The first terminal of the resistor R4 is connected to the source terminal S1 of the transistor T1. The second terminal of the resistor R4 is connected to a pad VOUT.

The inverter 131 includes an input terminal and an output terminal. The input terminal of the inverter 131 is connected to the pad VOUT. The output terminal of the inverter 131 is connected to the CDR circuit 120c.

The clock control signal output from the processor 6c is input to the CDR circuit 120c. The clock control signal in the fourth embodiment is a pulse signal having a cycle that is integer times longer than the cycle of the system clock of the processor 6c. The clock control signal has a first electric potential that is not included in a range of a signal level of the image data output to the signal line LS. The CDR circuit 120c adjusts a frequency of a camera clock by synchronizing the camera clock with the pulse signal. When the pattern of the pulse signal is a predetermined pattern, the CDR circuit 120c outputs data for switching the communication modes from the second mode to the first mode to the communication control circuit 103c.

The communication control circuit 103c is connected to the pad VOUT. The communication control circuit 103c detects the electric potential of the signal line LS. The communication control circuit 103c controls the multiplexer 130 on the basis of the electric potential of the signal line LS. The communication control circuit 103c outputs a mode-setting signal for setting the communication mode in the CDR circuit 120c to the CDR circuit 120c.

When the communication control circuit 103c detects the first electric potential higher than the maximum value of the third electric potential in the first mode, the communication control circuit 103c causes the input of the image data to the gate terminal G1 of the transistor T1 to the stopped and causes the input of the ground voltage (substrate voltage) to the gate terminal G1 of the transistor T1 to be started. Specifically, the communication control circuit 103c sets the state of the multiplexer 130 to the second state. In this way, the communication control circuit 103c switches the communication modes from the first mode to the second mode.

The communication control circuit 103c causes the input of the ground voltage (substrate voltage) to the gate terminal G1 of the transistor T1 to be stopped and causes the input of the image data to the gate terminal G1 of the transistor T1 to be started on the basis of the output of predetermined data from the CDR circuit 120c. Specifically, when the predetermined data are output front the CDR circuit 120c, the communication control circuit 103c starts counting of the camera clock. When a predetermined number is counted, the communication control circuit 103c sets the state of the multiplexer 130 to the first state. In this way, the communication control circuit 103c switches the communication modes from the second mode to the first mode.

The camera unit 10c includes a pad VDD3, a pad GND3, and the pad VOUT in addition to the imager 11 and the like. The pad VDD3 is connected to a power source line LV. The power source voltage is input to the pad VDD3. The pad GND3 is connected to a ground line LG. The ground voltage is input to the pad GND3.

The pad VOUT is connected to the second terminal of the resistor R4, the input terminal of the inverter 131, and the communication control circuit 103c. In addition, the pad VOUT is connected to the signal line LS. When the communication mode is the first mode, the image data are output from the resistor R4 and are input to the pad VOUT. The image data are output to the signal line LS via the pad VOUT. When the communication mode is the second mode, the clock control signal is input from the signal line LS to the pad VOUT. The clock control signal is output to the CDR circuit 120c via the pad VOUT and the inverter 131. In addition, the clock control signal is output to the communication control circuit 103c via the pad VOUT.

The camera unit 10c is electrically connected to the processor 6c via only the pad VOUT, the pad VDD3, and the pad GND3. Other than these three pads, no pads electrically connecting the camera unit 10c and the processor 6c together are disposed in the camera unit 10c.

The processor 6c includes an image reception circuit 60c and a power source circuit 62. When the communication mode is the first mode, the image reception circuit 60c receives the image data transmitted by the camera unit 10c. The received image data are output to a subsequent-stage circuit such as an analog front-end (AFE). When the communication mode is the second mode, the signal output circuit 61c outputs the clock control signal to the signal line LS. The image reception circuit 60c and the signal output circuit 61c operate on the basis of the system clock of the processor 6c. The power source circuit 62 outputs the power source voltage to the power source line LV and outputs the ground voltage to the ground line LG.

The image reception circuit 60c includes the signal output circuit 61c, a switch 600 (first switch), and a resistor RT1. The signal output circuit 61c includes a switch 610 and an inverter 611.

The inverter 611 includes an input terminal and an output terminal. A clock control signal CS is input to the input terminal of the inverter 611. The output terminal of the inverter 611 is connected to the switch 610. The clock control signal CS is input to the switch 610 via the inverter 611.

The switch 610 includes a first terminal and a second terminal. The clock control signal is input to the first terminal of the switch 610. The second terminal of the switch 610 is connected to the signal line LS. When the communication mode is the second mode, the state of the switch 610 becomes the ON state. At this time, the clock control signal is output to the signal line LS. When the communication mode is the first mode, the state of the switch 610 becomes the OFF state. At this time, the clock control signal is not output to the signal line LS. The state of the switch 610 is controlled on the basis of the signal generated by inverting a switch control signal SWCTL.

The resistor RT1 is a direct current (DC) termination resistor that operates when the image data are received. When the image reception circuit 60c receives the image data, the switch 600 electrically connects the signal line LS and the resistor RT1 together. When the signal output circuit 61c outputs the first electric potential to the signal line LS, the switch 600 electrically disconnects the signal line LS and the resistor RT1 from each other.

The switch 600 includes a first terminal and a second terminal. The first terminal of the switch 600 is connected to the signal line LS and the second terminal of the switch 600 is connected to the resistor RT1. When the communication mode is the first mode, the state of the switch 600 becomes the ON state. At this time, the resistor RT1 is electrically connected to the signal line LS and operates as the DC termination resistor. When the communication mode is the second mode, the state of the switch 600 becomes the OFF state. At this time, the resistor RT1 is electrically disconnected from the signal line LS. The state of the switch 600 is controlled on the basis of the switch control signal SWCTL.

When the state of the switch 600 is the ON state, the state of the switch 610 is the OFF state. When the state of the switch 600 is the OFF state, the state of the switch 610 is the ON state.

The resistor RT1 includes a first terminal and a second terminal. The first terminal of the resistor RT1 is connected to the second terminal of the switch 600. The ground voltage is input to the second terminal of the resistor RT1.

After the signal output circuit 61c outputs the first electric potential to the signal line LS, the signal output circuit 61c outputs the communication control signal indicating an instruction for switching the communication modes from the second mode to the first mode to the signal line LS. Specifically, the signal output circuit 61c outputs the clock control signal having a predetermined digital value to the signal line LS at a predetermined timing in a horizontal blanking period. The digital value indicates the switching of the communication modes. The clock control signal having the digital value corresponds to the communication control signal. The clock control signal includes a pattern of a high level and a low level. The pattern of the clock control signal corresponds to the data of the communication control signal.

Figure 11:
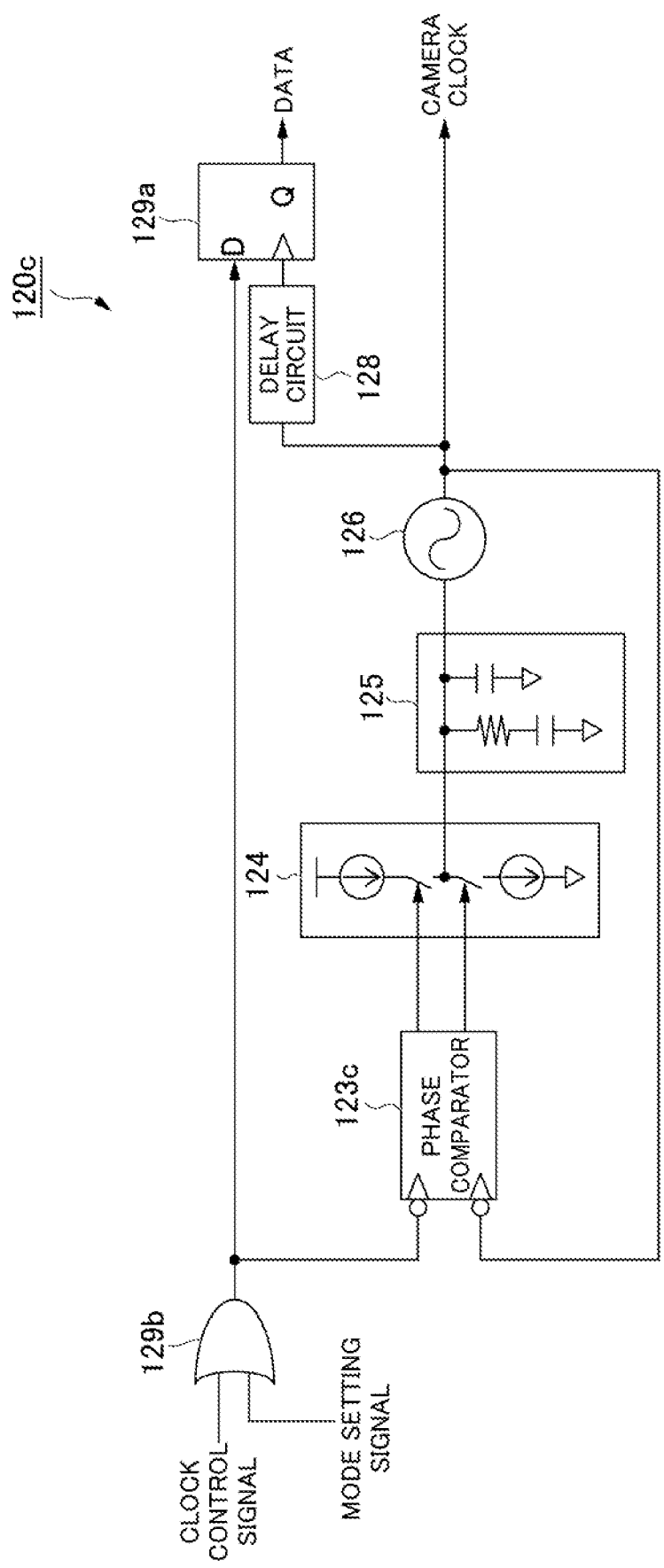
FIG. 11 is a block diagram showing a configuration of a CDR circuit included in the endoscope system according to the fourth embodiment of the present invention.

FIG. 11 shows a configuration of the CDR circuit 120c. The same parts as those shown in FIG. 8 will not be described. The CDR circuit 120c shown in FIG. 11 includes a phase comparator 123c, a charge pump 124, a loop filter 125, a VCO 126, a delay circuit 128, a logic circuit 129a, and a logic circuit 129b.

The logic circuit 129b is an OR circuit. The clock control signal and the mode-setting signal are input to the logic circuit 129b. The clock control signal is output from the signal line LS via the inverter 131. The mode-setting signal is output from the communication control circuit 103c. When the communication mode is the second mode, the mode-setting signal is set in the low level. At this time, the logic circuit 129b outputs the clock control signal. When the communication mode is the first mode, the mode-selling signal is set in the high level. At this time, the logic circuit 129b outputs a signal having the high level.

The signal output from the logic circuit 129b and the camera clock output from the VCO 126 are input to the phase comparator 123c. When the communication mode is the second mode, the clock control signal is output from the logic circuit 129b to the phase comparator 123c. The phase comparator 123c outputs a signal in accordance with the shift of the phase and the shift of the frequency between the clock control signal and the camera clock to the charge pump 124. The VCO 126 generates the camera clock having a frequency corresponding to the control voltage output from the loop filter 125.

When the communication mode is the first mode, the signal having the high level is output from the logic circuit 129b to the phase comparator 123c. The phase comparator 123c stops comparing the phase of the clock control signal with the phase of the camera clock. Therefore, the frequency of the camera clock output from the VCO 126 does not change.

The delay circuit 128 delays the camera clock output from the VCO 126. The delay circuit 128 outputs the delayed camera clock to the logic circuit 129a.

The logic circuit 129a is a D flip-flop. The logic circuit 129a takes in the clock control signal at a rising edge of the delayed camera clock and outputs a digital signal indicating the data. When the clock control signal is in the high level, the logic circuit 129a outputs the high level. When the clock control signal is in the low level, the logic circuit 129a outputs the low level.

Figure 12:
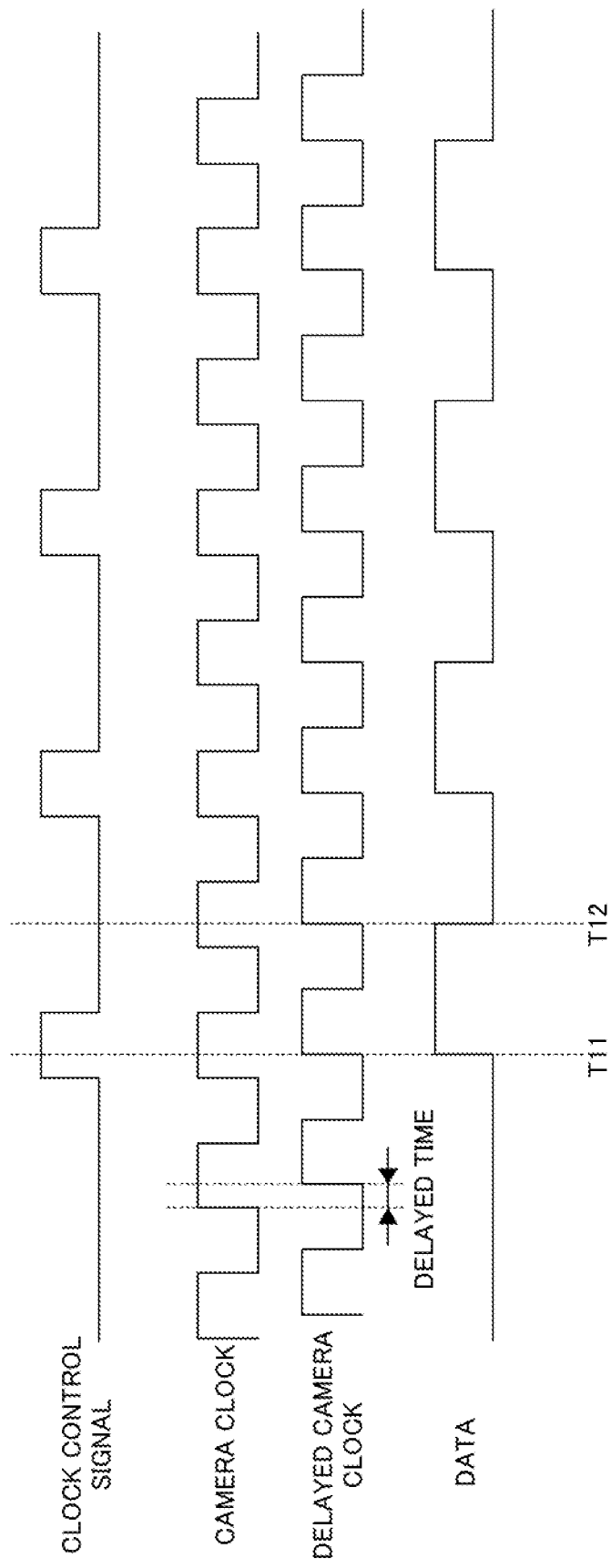
FIG. 12 is a timing chart showing an operation of the CDR circuit included in the endoscope system according to the fourth embodiment of the present invention.

FIG. 12 shows an operation of the COR circuit 120c regarding generation of the data. Time passes in the right direction in FIG. 12. The clock control signal, the camera clock, the delayed camera clock, and the data are shown in FIG. 12.

The delayed camera clock rises up in a timing T11. The logic circuit 129a takes in the clock control signal at the timing T11. The signal level of the clock control signal is the high level at the timing T11. The logic circuit 129a outputs the high level at the timing T11.

The delayed camera clock rises up in a timing T12. The logic circuit 129a takes in the clock control signal at the timing T12. The signal level of the clock control signal is the low level at the timing T12. The logic circuit 129a outputs the low level at the timing T12.

The CDR circuit 120c generates the data on the basis of the pattern of the pulse of the clock control signal by executing the above-described operation.

A method of generating the data on the basis of the pattern of the pulse of the clock control signal is not limited to the above-described method. For example, a method of generating a signal having a frequency that is double the frequency of the camera clock and taking in the clock control signal at a falling edge of the generated signal may be used.

Figure 13:
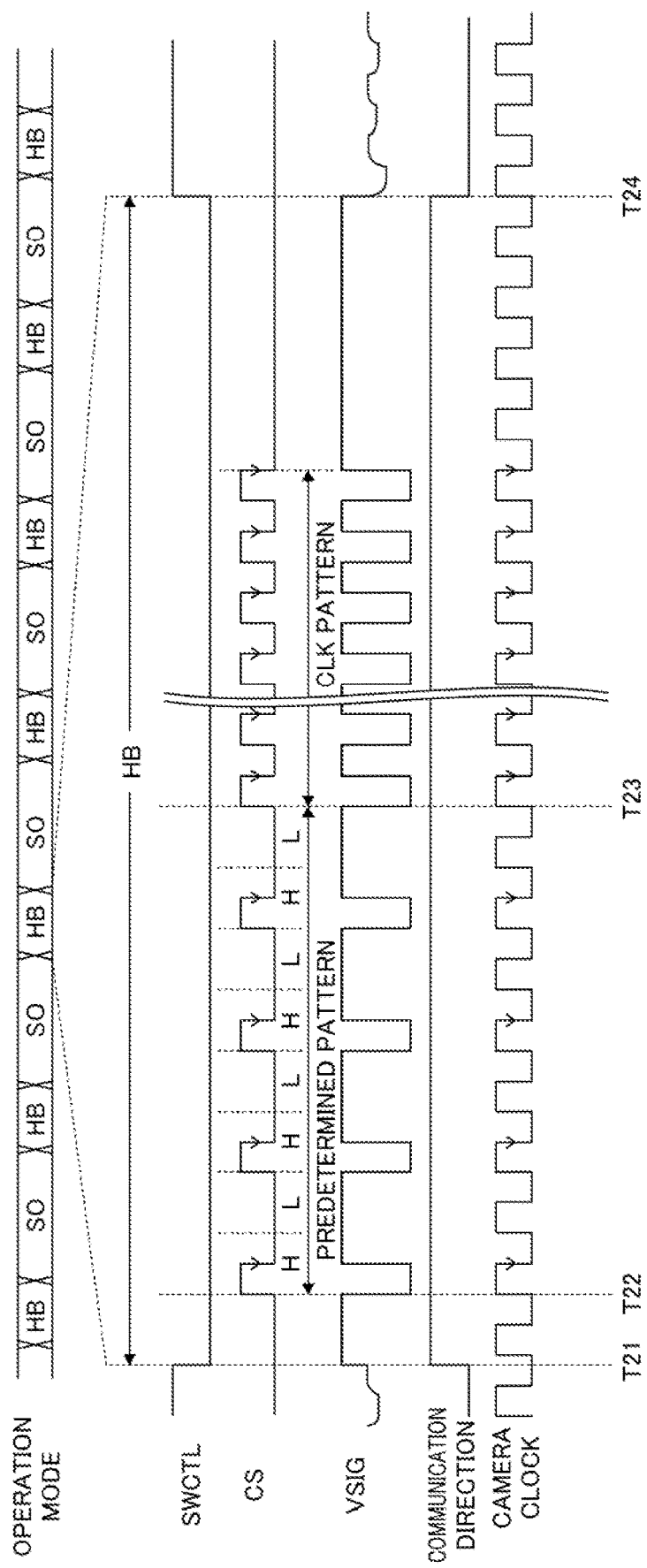
FIG. 13 is a timing chart of communication in the endoscope system according to the fourth embodiment of the present invention.

FIG. 13 shows timings of communication in the endoscope system 1c. Time passes in the right direction in FIG. 13. The operation mode of the imager 11, the switch control signal SWCTL, the clock control signal CS, the electric potential (VSIG) of the signal line LS, the communication direction, and the camera clock are shown in FIG. 13. The signal level of the clock control signal CS shown in FIG. 13 is the signal level of the signal input to the input terminal of the inverter 611.

The imager 11 repeats an operation in a signal-output period (SO) and an operation in a horizontal blanking period (HB). Each of the signals in the enlarged horizontal blanking period (HB) is shown in FIG. 13.

In the signal-output period (SO), the switch control signal SWCTL is in the high level. At this time, the state of the switch 600 is the ON state and the state of the switch 610 is the OFF state. The communication mode is the first mode.

When the horizontal blanking period (HB) is started, the signal level of the switch control signal SWCTL changes from the high level to the low level. At this time, the state of the switch 600 becomes the OFF state and the state of the switch 610 becomes the ON state. When the horizontal blanking period (HB) is started, the signal level of the clock control signal CS is the low level. Therefore, the signal output circuit 61c outputs the clock control signal of the high level to the signal line LS.

When the clock control signal is output to the signal line LS, the electric potential of the signal line LS is pulled up to the first electric potential. For example, the first electric potential is the power source voltage. The communication control circuit 103c detects the first electric potential at a timing T21 and sets the state of the multiplexer 130 to the second state. In this way, the communication control circuit 103c switches the communication modes from the first mode to the second mode. The ground voltage is input to the gate terminal G1 of the transistor T1 of the buffer 101c.

From a timing T22, the pulse signal having a predetermined pattern is input to the input terminal of the inverter 611 as the clock control signal CS. The predetermined pattern is configured by a combination of the high level and the low level. In the example shown in FIG. 13, the predetermined pattern is "HLHLHLHL." The signal output circuit 61c outputs the clock control signal generated by inverting the clock control signal CS to the signal line LS. The CDR circuit 120c generates data corresponding to the pattern of the clock control signal CS and outputs the data to the communication control circuit 103c.

After the pulse signal having the predetermined pattern is output, the pulse signal having a cycle that is integer times longer than the cycle of the system clock of the processor 6c is input to the input terminal of the inverter 611 as the clock control signal CS. The signal output circuit 61c outputs the clock control signal generated by inverting the clock control signal CS to the signal line LS. The VCO 126 of the CDR circuit 120c generates rite camera clock having a frequency of the clock control signal.

The communication control circuit 103c detects data corresponding to the predetermined pattern of the clock control signal and starts the counting at a timing T23. When a predetermined number is counted, the communication control circuit 103c sets the state of the multiplexer 130 to the first state at a timing T24. In this way, the communication control circuit 103c switches the communication modes from the second mode to the first mode. The image data are input to the gate terminal G1 of the transistor T1. At the timing T24, the horizontal blanking period (HB) is completed and the signal-output period (SO) is started.

The buffer 101c does not need to include the resistor R4 and the source terminal S1 of the transistor T1 may be connected to the pad VOUT. In this case, the maximum value of the third electric potential corresponding to the signal level of the image data is lower than the power source voltage by the threshold voltage of the transistor T1. In the example shown in FIG. 10, since the resistor R4 is connected to the source terminal S1 of the transistor T1, a voltage drop in the resistor R4 occurs. Therefore, the difference between the first electric potential (power source voltage) and the maximum value of the third electric potential becomes large. Consequently, the communication control circuit 103c easily detects the first electric potential.

In the fourth embodiment, the signal output circuit 61c outputs the first electric potential (power source voltage) to the signal line LS. The first electric potential corresponds to the signal level that is not included in the range of the signal level of the image data output to the signal line LS. When the communication control circuit 103c detects the first electric potential in the first mode, the communication control circuit 103c switches the communication modes front the first mode to the second mode. Since switching of the communication modes is controlled on the basis of the signal output from the processor 6c, the endoscope system 1c can improve the accuracy of the operation of switching the communication modes.

When the signal output circuit 61c outputs the first electric potential to the signal line LS, the resistor RT1 is electrically disconnected from the signal line LS. Therefore, the communication control circuit 103c can switch the communication modes without causing an increase of an unnecessary current.

Modified Example of Fourth Embodiment

Figure 14:
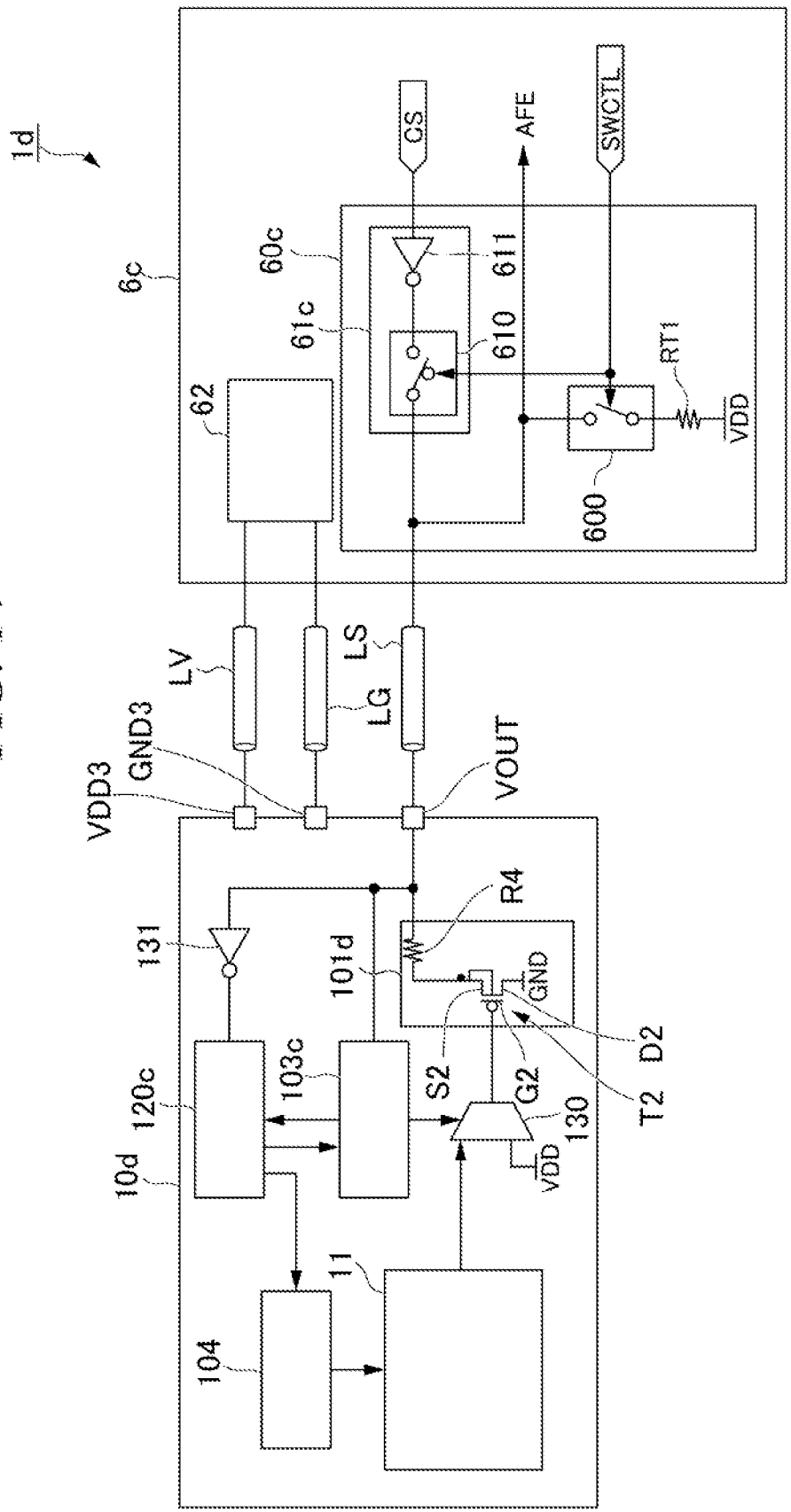
FIG. 14 is a block diagram showing a configuration of an endoscope system according to a modified example of the fourth embodiment of the present invention.

FIG. 14 shows an internal configuration of an endoscope system 1d according to a modified example of a fourth embodiment. The same parts as those shown in FIG. 10 will not be described.

The endoscope system 1d includes a camera unit 10d and a processor 6c. The camera unit 10d includes an imager 11, a buffer 101d, a communication control circuit 103c, a timing generator 104, a CDR circuit 120c, a multiplexer 130, and an inverter 131.

The buffer 101d includes a transistor T2 and a resistor R4. The buffer 101d is a source follower circuit.

The transistor T2 includes a gate terminal G2 (first terminal), a drain terminal D2 (second terminal), and a source terminal S2 (third terminal). The gate terminal G2 is connected to the output terminal of the multiplexer 130. The image data or the power source voltage is input to the gate terminal G2. The ground voltage GND (substrate voltage) is input to the drain terminal D2. The first terminal of the resistor R4 is connected to the source terminal S2 of the transistor T2.

When the communication mode is the first mode, the image data are input to the gate terminal G2. The source terminal S2 outputs a third electric potential corresponding to a signal level of the image data to a signal line LS via the resistor R4. The maximum value of the third electric potential is less than or equal to the power source voltage. The minimum value of the third electric potential is greater than or equal to the voltage higher than the ground voltage GND (substrate voltage) by the threshold voltage of the transistor T2.

When the communication mode is the second mode, the power source voltage is input to the gate terminal G2. The state of the transistor T2 becomes the OFF state. Therefore, the output of the image data to the signal line LS is stopped.

When the communication control circuit 103c detects the first electric potential lower than the minimum value of the third electric potential in the first mode, the communication control circuit 103c causes the input of the image data to the gate terminal G2 of the transistor T2 to be stopped and causes the input of the power source voltage to the gate terminal G2 of the transistor T2 to be started. Specifically, the communication control circuit 103c sets the state of the multiplexer 130 to the second state. In this way, the communication control circuit 103c switches the communication modes from the first mode to the second mode.

The communication control circuit 103c causes the input of the power source voltage to the gate terminal G2 of the transistor T2 to be stopped and causes the input of the image data to the gate terminal G2 of the transistor T2 to be started on the basis of the output of predetermined data from the CDR circuit 120c. Specifically, when the predetermined data are output from the CDR circuit 120c, the communication control circuit 103c starts counting of the camera clock. When a predetermined number is counted, the communication control circuit 103c sets the state of the multiplexer 130 to the first state. In this way, the communication control circuit 103c switches the communication modes from the second mode to the first mode.

The power source voltage VDD is input to the second terminal of the resistor RT1. The processor 6c shown in FIG. 14 is the same as the processor 6c shown in FIG. 10, excluding this point.

When the horizontal blanking period (HB) is started and the clock control signal is output to the signal line LS, the electric potential of the signal line LS is pulled down to the first electric potential. For example, the first electric potential is the ground voltage GND. The communication control circuit 103c detects the first electric potential and switches the communication modes from the first mode to the second mode.

Fifth Embodiment

Figure 15:
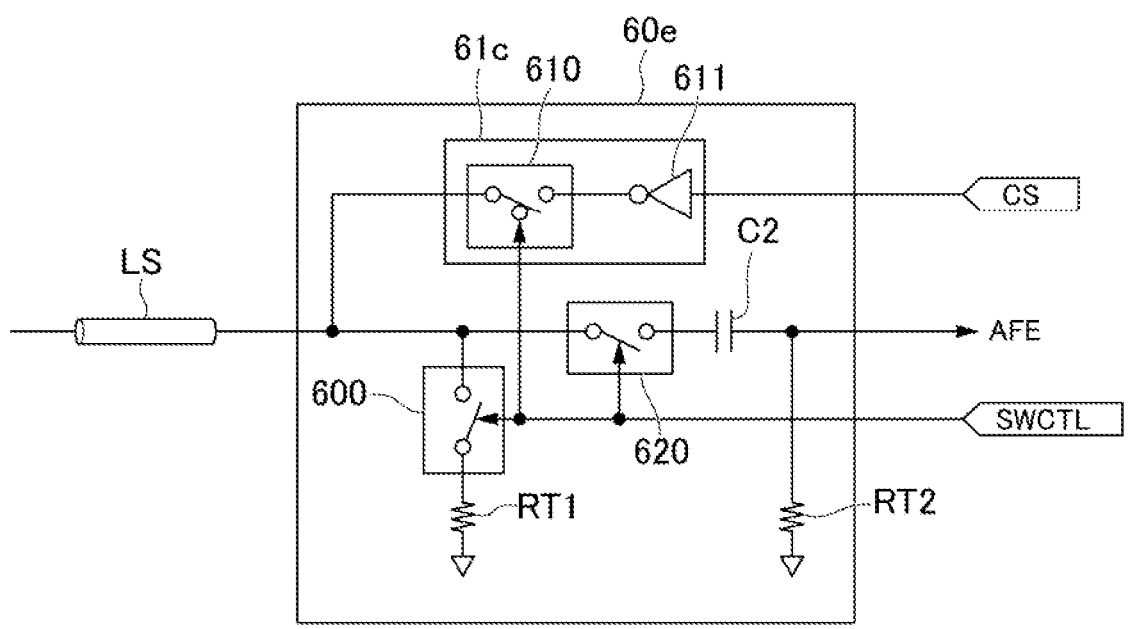
FIG. 15 is a block diagram showing a configuration of an image reception circuit included in an endoscope system according to a fifth embodiment of the present invention.

FIG. 15 shows a configuration of an image reception circuit 60e included in an endoscope system according to a fifth embodiment of the present invention. The same parts as those shown in FIG. 10 will not be described.

The image reception circuit 60e shown in FIG. 15 includes a signal output circuit 61c, a switch 600 (first switch), a switch 620 (second switch), a resistor RT1, a resistor RT2, and a capacitance element C2 (DC-cutting condenser).

The resistor RT2 is an alternating current (AC) termination resistor that operates when the image data are received. The capacitance element C2 is connected to a signal line LS and the resistor RT2. When the image data are received, the capacitance element C2 cuts DC components of the electric potential of the signal line LS. When the image reception circuit 60e receives the image data, the switch 620 electrically connects the signal line LS and the resistor RT2 together and electrically connects the signal line LS and the capacitance element C2 together. When the signal output circuit 61c outputs the first electric potential to the signal line LS, the switch 620 electrically disconnects the signal line LS and the resistor RT2 from each other and electrically disconnects the signal line LS and the capacitance element C2 from each other.

The switch 620 includes a first terminal and a second terminal. The first terminal of the switch 620 is connected to the signal line LS and the second terminal of the switch 620 is connected to the capacitance element C2. When the communication mode is the first mode, the state of the switch 620 becomes the ON state. At this time, the resistor RT2 and the capacitance element C2 are electrically connected to the signal line LS. The resistor RT2 operates as an AC termination resistor and the capacitance element C2 operates as a DC-cutting condenser. When the communication mode is the second mode, the state of the switch 620 becomes the OFF state. At this time, the resistor RT2 and the capacitance element C2 are electrically disconnected from the signal line LS. The state of the switch 620 is controlled on the basis of a switch control signal SWCTL.

When the state of each of the switch 600 and the switch 620 is the ON state, the state of the switch 610 is the OFF state. When the state of each of the switch 600 and the switch 620 is the OFF state, the state of the switch 610 is the ON state.

The capacitance element C2 includes a first terminal and a second terminal. The first terminal of the capacitance element C2 is connected to the second terminal of the switch 620. The second terminal of the capacitance element C2 is connected to the resistor RT2.

The resistor RT2 includes a first terminal and a second terminal. The first terminal of the resistor RT2 is connected to the second terminal of the capacitance element C2. The ground voltage is input to the second terminal of the resistor RT2.

When the communication mode is the first mode, the electric charge that is based on the DC voltage between the two terminals of the capacitance element C2 is accumulated in the capacitance element C2. In a case in which the image reception circuit is configured so that the capacitance element C2 is connected to the signal line LS at all times, the DC voltage between the two terminals of the capacitance element C2 is different between the first mode and the second mode. When the communication modes are switched with the capacitance element C2 being connected to the signal line LS, it takes some time until the DC voltage between the two terminals of the capacitance element C2 stabilizes.

In the image reception circuit 60e shown in FIG. 15, when the communication mode is the second mode, the capacitance element C2 is electrically disconnected from the signal line LS. The electric charge accumulated in the capacitance element C2 in the first mode is held in the capacitance element C2 in the second mode. When the communication modes are switched front the second mode to the first mode, the capacitance element C2 is electrically connected to the signal line LS. At this time, the DC voltage between the two terminals of the capacitance element C2 tends to stabilize quickly. Therefore, the endoscope system can quickly start stable communication of the image data.

While preferred embodiments of the invention have been described and shown above, it should be understood that these are examples of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An imaging system, comprising:
a camera unit comprising:
an imager configured to generate image data on the basis of a camera clock;
a communication control circuit configured to detect an electric potential of a signal line and switch communication modes between a first mode and a second mode on the basis of the detected electric potential;
an image transmission circuit configured to output the image data to the signal line in the first mode;
a signal reception circuit that is electrically connected to the signal line and is configured to receive a clock control signal for adjusting a frequency of the camera clock from the image reception unit in the second mode; and
a clock adjustment circuit configured to adjust the frequency of the camera clock on the basis of the clock control signal, and
an image reception unit comprising:
an image reception circuit that is electrically connected to the signal line and is configured to receive the image data; and
a signal output circuit configured to output a first electric potential and the clock control signal to the signal line, the first electric potential corresponding to a signal level that is not included in a range of a signal level of the image data output to the signal line,
wherein the communication control circuit is configured to switch the communication modes from the first mode to the second mode when the communication control circuit detects the first electric potential in the first mode.

2. The imaging system according to claim 1,
wherein the signal output circuit is configured to output a communication control signal indicating an instruction to switch the communication modes from the second mode to the first mode to the signal line after the signal output circuit outputs the first electric potential to the signal line, and
the communication control circuit is configured to switch the communication modes from the second mode to the first mode when the communication control circuit detects the communication control signal on the signal line in the second mode.

3. The imaging system according to claim 2,
wherein the clock control signal is a pulse signal indicating a system clock of the image reception unit, and
a pattern of a signal level of the pulse signal corresponds to data of the communication control signal.

4. The imaging system according to claim 1,
wherein the signal output circuit is configured to output a second electric potential to the signal line after the signal output circuit outputs the first electric potential to the signal line, the second electric potential corresponding to a signal level included in the range of the signal level of the image data, and
the communication control circuit is configured to switch the communication modes from the second mode to the first mode when the communication control circuit detects the second electric potential in the second mode.

5. The imaging system according to claim 1,
wherein the camera unit and the image reception unit are connected to each other by the signal line, a first power source line, and a second power source line,
the first power source line is configured to transmit a power source voltage that is to be supplied to the imager from the image reception unit to the camera unit,
the second power source line is configured to transmit a substrate voltage that is to be supplied to the imager from the image reception unit to the camera unit, the substrate voltage being lower than the power source voltage,
the camera unit further comprises:
a first pad electrically connected to the signal line;
a second pad electrically connected to the first power source line; and
a third pad electrically connected to the second power source line, and
the camera unit is electrically connected to the image reception unit via only the first pad, the second pad, and the third pad.

6. The imaging system according to claim 5,
wherein the image transmission circuit includes a source follower circuit including a transistor,
the transistor comprises:
a first terminal to which the image data or the substrate voltage is input;
a second terminal to which the power source voltage is input; and
a third terminal,
the image data are input to the first terminal in the first mode,
the third terminal outputs a third electric potential corresponding to the signal level of the image data to the signal line in the first mode,
a maximum value of the third electric potential is less than or equal to a voltage lower than the power source voltage by a threshold voltage of the transistor,
a minimum value of the third electric potential is greater than or equal to the substrate voltage, and
the communication control circuit is configured to switch the communication modes from the first mode to the second mode by causing input of the image data to the first terminal to be stopped and causing input of the substrate voltage to the first terminal to be started when the communication control circuit detects the first electric potential higher than the maximum value in the first mode.

7. The imaging system according to claim 5,
wherein the image transmission circuit includes a source follower circuit including a transistor,
the transistor comprises:
a first terminal to which the image data or the substrate voltage is input;
a second terminal to which the substrate voltage is input; and
a third terminal,
the image data are input to the first terminal in the first mode,
the third terminal outputs a third electric potential corresponding to the signal level of the image data to the signal line in the first mode,
a maximum value of the third electric potential is less than or equal to the power source voltage, a minimum value of the third electric potential is greater than or equal to a voltage higher than the substrate voltage by a threshold voltage of the transistor, and the communication control circuit is configured to switch the communication modes from the first mode to the second mode by causing input of the image data to the first terminal to be stopped and causing input of the power source voltage to the first terminal to be started when the communication control circuit detects the first electric potential lower than the minimum value in the first mode.

8. The imaging system according to claim 1, further comprising a first switch, wherein the image reception circuit includes a DC termination resistor configured to operate when the image data are received, the first switch is configured to electrically connect the signal line and the DC termination resistor together when the image reception circuit receives the image data, and the first switch is configured to electrically disconnect the signal line and the DC termination resistor from each other when the signal output circuit outputs the first electric potential to the signal line.

9. The imaging system according to claim 8, further comprising a second switch, wherein the image reception circuit comprises:
an AC termination resistor; and
a DC-cutting condenser that is connected to the signal line and the AC termination resistor and is configured to cut DC components of an electric potential of the signal line when the image data are received, the second switch is configured to electrically connect the signal line and the AC termination resistor together and electrically connect the signal line and the DC-cutting condenser together when the image reception circuit receives the image data, and the second switch is configured to electrically disconnect the signal line and the AC termination resistor from each other and electrically disconnect the signal line and the DC-cutting condenser from each other when the signal output circuit outputs the first electric potential to the signal line.

10. The imaging system according to claim 1,
wherein the signal output circuit is configured to output the clock control signal to the signal line in a blanking period of the imager.

11. The imaging system according to claim 1,
wherein the signal output circuit is configured to output a negative voltage that is not included in the range of the signal level of the image data to the signal line, and the camera unit further comprises a voltage supply circuit that is electrically connected to the signal line and is configured to supply the negative voltage to the imager in the second mode.

12. The imaging system according to claim 11,
wherein the signal output circuit is configured to output the negative voltage to the signal line in a horizontal blanking period of the imager and output the clock control signal to the signal line in a vertical blanking period of the imager.

13. The imaging system according to claim 1,
wherein the clock control signal is a pulse signal having a cycle that is integer times longer than a cycle of a system clock of the image reception unit, and the clock adjustment circuit is configured to synchronize the camera clock with the pulse signal.

14. The imaging system according to claim 1,
wherein the clock control signal is an analog signal having a voltage corresponding to a frequency of a system clock of the image reception unit, and the clock adjustment circuit includes a voltage-controlled oscillator (VCO) configured to generate the camera clock having a frequency corresponding to a voltage of the clock control signal.

15. The imaging system according to claim 1,
wherein the clock control signal is a digital signal indicating a value corresponding to a frequency of a system clock of the image reception unit, and the clock adjustment circuit comprises:
a digital-to-analog converter (DAC) circuit configured to generate an analog signal having a voltage corresponding to the value indicated by the clock control signal; and
a voltage-controlled oscillator (VCO) configured to generate the camera clock having a frequency corresponding to the voltage of the analog signal.

* * * * *